(12) United States Patent
Kegnæs et al.

(10) Patent No.: US 10,265,686 B2
(45) Date of Patent: *Apr. 23, 2019

(54) METHOD OF PRODUCING ZEOLITE ENCAPSULATED NANOPARTICLES

(71) Applicant: Danmarks Tekniske Universitet, Kgs. Lyngby (DK)

(72) Inventors: Søren Kegnæs, Limhamn (SE); Jacob Oskar Abildstrøm, København K (DK); Jerrik Jørgen Mielby, Vanløse (DK); Agata Gallas-Hulin, Holte (DK)

(73) Assignee: DANMARKS TEKNISKE UNIVERSITET, KGS. Lyngby (DK)

( * ) Notice: Subject to any disclaimer, the term of this patent is extended or adjusted under 35 U.S.C. 154(b) by 301 days.

This patent is subject to a terminal disclaimer.

(21) Appl. No.: 14/899,460

(22) PCT Filed: Jul. 7, 2014

(86) PCT No.: PCT/EP2014/064428
§ 371 (c)(1),
(2) Date: Dec. 17, 2015

(87) PCT Pub. No.: WO2015/001122
PCT Pub. Date: Jan. 8, 2015

(65) Prior Publication Data
US 2016/0129429 A1 May 12, 2016

(30) Foreign Application Priority Data
Jul. 5, 2013 (EP) .................................... 13175324

(51) Int. Cl.
*B01J 29/06* (2006.01)
*B01J 29/064* (2006.01)
*B01J 29/04* (2006.01)
*B01J 35/10* (2006.01)
*B01J 37/00* (2006.01)
*B01J 29/89* (2006.01)
*C01B 39/08* (2006.01)
*C01B 37/00* (2006.01)
(Continued)

(52) U.S. Cl.
CPC ........... *B01J 29/064* (2013.01); *B01J 29/041* (2013.01); *B01J 29/042* (2013.01); *B01J 29/043* (2013.01); *B01J 29/044* (2013.01); *B01J 29/045* (2013.01); *B01J 29/076* (2013.01); *B01J 29/89* (2013.01); *B01J 35/109* (2013.01); *B01J 35/1061* (2013.01); *B01J 35/1066* (2013.01); *B01J 37/0018* (2013.01); *B01J 37/10* (2013.01); *B01J 37/16* (2013.01); *C01B 37/005* (2013.01); *C01B 39/085* (2013.01); *C01B 39/40* (2013.01); *C07C 2/66* (2013.01); *C07C 5/2737* (2013.01); *B01J 2229/183* (2013.01); *B01J 2229/186* (2013.01); *B01J 2229/60* (2013.01); *C07C 2529/04* (2013.01); *C07C 2529/068* (2013.01); *C07C 2529/072* (2013.01); *C07C 2529/076* (2013.01)

(58) Field of Classification Search
CPC ........ B01J 29/89; B01J 29/041; B01J 29/042; B01J 29/043; B01J 29/044; B01J 29/045; B01J 2229/60; B01J 2229/183; B01J 35/1061; B01J 35/109; B01J 37/0018; B01J 2229/186; C07C 2529/89; C07C 2529/04; C07C 2529/068; C07C 2529/072; C07C 2529/076
USPC ...................................................... 502/60, 74
See application file for complete search history.

(56) References Cited

U.S. PATENT DOCUMENTS

| 4,410,501 A | 10/1983 | Taramasso et al. | |
|---|---|---|---|
| 2003/0139283 A1* | 7/2003 | Herbst ................... | B01J 29/061 502/64 |

(Continued)

FOREIGN PATENT DOCUMENTS

| CN | 101538049 A | 9/2009 |
|---|---|---|
| CN | 201310208234 | * 5/2013 |

(Continued)

OTHER PUBLICATIONS

Goel et al., "Synthesis and Catalytic Consequences of Metal and Oxide Clusters Encapsulated within Zeolites", 23rd North American Catalyst Society Meeting, Jun. 5, 2013.*

(Continued)

*Primary Examiner* — Elizabeth D Wood
(74) *Attorney, Agent, or Firm* — Knobbe, Martens, Olson & Bear, LLP

(57) ABSTRACT

The invention therefore relates to a method for producing zeolite, zeolite-like or zeotype encapsulated metal nanoparticles, the method comprises the steps of: 1) Adding one or more metal precursors to a silica or alumina source; 2) Reducing the one or more metal precursors to form metal nanoparticles on the surface of the silica or alumina source; 3) Passing a gaseous hydrocarbon, alkyl alcohol or alkyl ether over the silica or alumina supported metal nanoparticles to form a carbon template coated zeolite, zeolite-like or zeotype precursor composition; 4a) Adding a structure directing agent to the carbon template coated zeolite, zeolite-like or zeotype precursor composition thereby creating a zeolite, zeolite-like or zeotype gel composition; 4b) Crystallising the zeolite, zeolite-like or zeotype gel composition by subjecting said composition to a hydrothermal treatment; 5) Removing the carbon template and structure directing agent and isolating the resulting zeolite, zeolite-like or zeotype encapsulated metal nanoparticles.

7 Claims, 13 Drawing Sheets

Figure 1:
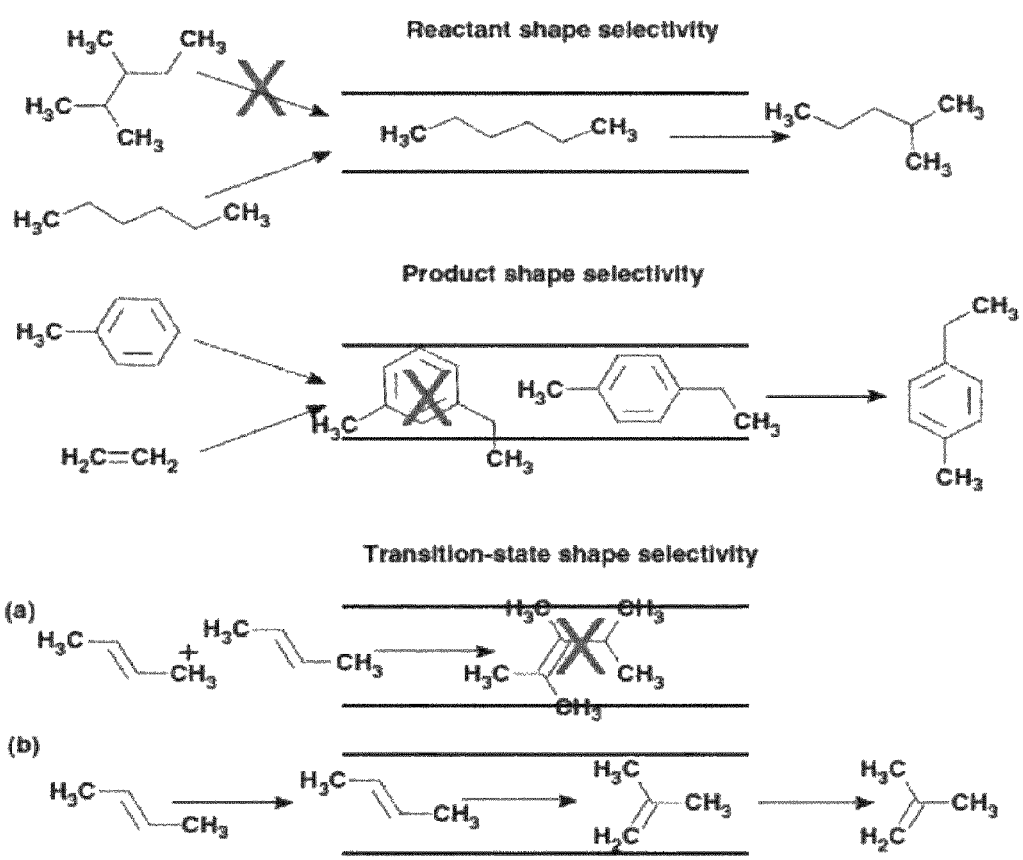

(51) Int. Cl.

| | |
|---|---|
| *C01B 39/40* | (2006.01) |
| *B01J 29/076* | (2006.01) |
| *B01J 37/10* | (2006.01) |
| *B01J 37/16* | (2006.01) |
| *C07C 2/66* | (2006.01) |
| *C07C 5/27* | (2006.01) |

(56) References Cited

U.S. PATENT DOCUMENTS

| | | | | |
|---|---|---|---|---|
| 2007/0258884 | A1* | 11/2007 | Pinnavaia | B01J 29/084 423/700 |
| 2011/0212020 | A1* | 9/2011 | Pinnavaia | B01J 29/084 423/700 |
| 2015/0151277 | A1* | 6/2015 | Tzeng | B01J 23/42 502/182 |
| 2016/0051971 | A1 | 2/2016 | Choi et al. | |

FOREIGN PATENT DOCUMENTS

| | | |
|---|---|---|
| JP | 2009-155178 A | 7/2009 |
| JP | 2011-184281 A | 9/2011 |
| JP | 2016-520419 | 7/2016 |
| JP | 2016-522657 | 7/2016 |
| KR | 10-2009-0124384 A | 12/2009 |
| WO | WO 2010/097108 | 9/2010 |
| WO | WO 2014/175626 | 10/2014 |
| WO | WO 2015/001123 A1 | 1/2015 |

OTHER PUBLICATIONS

Office Action in Chinese Patent Application No. 201480038182.X dated Jan. 17, 2017.

Janssen, A.H. et al., "Exploratory study of mesopore templating with carbon during zeolite synthesis" Microporous and Mesoporous Materials, 2003, pp. 59-75, vol. 65.

Pérez-Ramírez, Javier et al., "Hierarchical zeolites: enhanced utilization of microporous crystals in catalysis by advances in materials design" Chem. Soc. Rev., 2008, pp. 2530-2542, vol. 37.

Schmidt, Iver et al., "Carbon Nanotube Templated Growth of Mesoporous Zeolite Single Crystals" Chem. Mater., 2001, pp. 4416-4418, vol. 13.

Wang, Xiaoxing et al., "Synthesis, characterization and catalytic performance of hierarchical TS-1 with carbon template from sucrose carbonization" Microporous and Mesoporous Materials, 2011, pp. 494-502, vol. 142.

International Search Report for PCT/EP2014/064428 dated Sep. 10, 2014.

Office Action in Japanese Patent Application No. 2016-522656 dated Feb. 19, 2018.

Arnal et al., "High-Temperature-Stable Catalysts by Hollow Sphere Encapsulation" Angew. Chem. Int. Ed., 2006, vol. 45, pp. 8404-8407.

Beakley et al., "Nanocomposite catalysts: Dendrimer encapsulated nanoparticles immobilized in sol-gel silica" Applied Catalysis A: General, 2005, vol. 292, pp. 124-129.

Bordiga et al., "Reactivity of Ti(IV) species hosted in TS-1 towards $H_2O_2$—$H_2O$ solutions investigated by ab initio cluster and periodic approaches combined with experimental XANES and EXAFS data: a review and new highlights" Physical Chemistry Chemical Physics, 2007, vol. 9, pp. 4854-4878.

Broach, R.W. et al., "Zeolites" Ullmann's Encyclopedia of Industrial Chemistry, 2012, pp. 1-35.

Burgess et al., "The Lower Closure Point in Adsorption Hysteresis of the Capillary Condensation Type" J. Colloid Interface Sci., 1970, vol. 33, pp. 611-614.

Cavani et al., "Sustainability in Catalytic Oxidation: An Alternative Approach or a Structural Evolution?" ChemSusChem, 2009, vol. 2, pp. 508-534.

Cejka, J. et al., "Zeolites and other micro- and mesoporous molecular sieves", Kirk-Othmer Encyclopedia of Chemical Technology, 2010, pp. 1-30.

Corma et al., "Lewis Acids as Catalysts in Oxidation Reactions: From Homogeneous to Heterogeneous Systems" Chemical Reviews, 2002, vol. 102, pp. 3837-3892.

Dong et al., "Preparation of Hollow Zeolite Spheres and Three-Dimensionally Ordered Macroporous Zeolite Monoliths with Functionalized Interiors" Advanced Functional Materials, 2003, vol. 13, pp. 943-948.

Gao et al., "Characterization and catalytic tests of Au/MFI prepared by sublimation of $AuCl_3$ onto HMFI" Catalysis Letters, 2001, vol. 72, No. 1-2, pp. 1-5.

Groen et al., "Pore size determination in modified micro- and mesoporous materials. Pitfalls and limitations in gas adsorption data analysis" Microporous and Mesoporous Materials, 2003, vol. 60, pp. 1-17.

Højholt et al., "Size-Selective Oxidation of Aldehydes with Zeolite Encapsulated Gold Nanoparticles" Top Catal, 2001, vol. 54, pp. 1026-1033.

Jacobsen et al., "Mesoporous Zeolite Single Crystals" J. Am. Chem. Soc., 2000, pp. 7116-7117, vol. 122, No. 29.

Joo et al., "Thermally stable Pt/mesoporous silica core-shell nanocatalysts for high-temperature reactions" Nature Materials, 2009, vol. 8, pp. 126-131.

Kadlec et al., "Comments on the Limits of Applicability of the Mechanism of Capillary Condensation" J. Colloid Interface Sci., 1969, vol. 31, pp. 479-489.

Kang et al., "Preparation of gold in Y-type zeolite for carbon monoxide oxidation" Applied Catalysis A: General, 1995, vol. 128, pp. 53-60.

Kustova et al.,, "Versatile Route to Zeolite Single Crystals with Controlled Mesoporosity: in situ Sugar Decomposition for Templating of Hierarchical Zeolites" Chemistry of Materials, 2007, pp. 2915-2917, vol. 19, No. 12.

Laursen et al., "Substrate Size-Selective Catalysis with Zeolite-Encapsulated Gold Nanoparticles" Angew. Chem., 2010, vol. 122, pp. 3582-3585.

Petrini et al., "Deactivation Phenomena on Ti-Silicalite" Stud. Surf. Sci. Catal., 1991, vol. 68, pp. 761-766.

Ratnasamy et al., "Active Sites and Reactive Intermediates in Titanium Silicate Molecular Sieves" Advances in Catalysis, 2004, vol. 48, pp. 1-169.

Ren et al., "Novel, efficient hollow zeolitically microcapsulized noble metal catalysts" Journal of Catalysis, 2007, vol. 251, pp. 182-188.

Rovik et al., "Effect of alloying on carbon formation during ethane dehydrogenation" Applied Catalysis A: General, 2009, vol. 358, pp. 269-278.

Salama et al.,"Highly Selective Catalytic Reduction of NO by $H_2$ over Au° and Au(I) Impregnated in NaY Zeolite Catalysts" Journal of Catalysis, 1996, vol. 162, pp. 169-178.

Saxton, "Crystalline microporous titanium silicates" Topics in Catalysis, 1999, vol. 9, pp. 43-57.

Sehested, "Four challenges for nickel steam-reforming catalysts" Catalysis Today, 2006, vol. 111, pp. 103-110.

Sing, "Reporting physisorption data for gas/solid systems" Pure & Appl. Chem., 1982, vol. 54, No. 11, pp. 2201-2218.

Smart et al., Solid State Chemistry—An Introduction, CRC Press, 3rd Edition, 2005.

Spangsberg Holm, "Conversion of Oxygenates over Zeolite Catalysts : Structure-Activity Relations" Ph.D. Thesis, Department of Chemistry, Technical University of Denmark, 2011, pp. 1-132.

Vayssilov, "Structural and Physicochemical Features of Titanium Silicalites" Catalysis Reviews, 1997, vol. 39, pp. 209-251.

Wang et al., "Cobalt nanoparticles prepared in faujasite zeolites by borohydride reduction," Microporous and Mesoporous Materials, 2005, vol. 86, pp. 38-49.

Warnken et al., "Redox behaviour of $SnO_2$ nanoparticles encapsulated in the pores of zeolites towards reductive gas atmospheres studied by in situ diffuse reflectance UV/Vis and Mossbauer spectroscopy" Phys. Chem. Chem. Phys. 2001, vol. 3, pp. 1870-1876.

(56) References Cited

OTHER PUBLICATIONS

Yoon et al., "A Highly Reactive and Sinter-Resistant Catalytic System Based on Platinum Nanoparticles Embedded in the Inner Surfaces of CeO2 Hollow Fibers" Angew. Chem., 2012, vol. 124, pp. 9681-9684.
Zhao et al., "Encapsulation of Transition Metal Species into Zeolites and Molecular Sieves as Redox Catalysts: Part ImPreparation and Characterisation of Nanosized TiO2, CdO and ZnO Semiconductor Particles Anchored in NaY Zeolite" Journal of Porous Materials, 1996, vol. 3, pp. 61-66.
Zhu et al., "Encapsulation of Metal (Au, Ag, Pt) Nanoparticles into Mesoporous SBA-15 structure" Langmuir, 2003, vol. 19, pp. 4396-4401.
Zhu et al., "Tailoring the porosity of hierarchical zeolites by carbon-templating" Studies in Surface Science and Catalysis, 2008, pp. 285-288.
Office Action in Chinese Patent Application No. 201480038193.8 dated Jan. 24, 2017.
Burton et al., "SSZ-53 and SSZ-59: Two Novel Extra-Large Pore Zeolites" Chem. Eur. J., 2003, vol. 9, pp. 5737-5748.
Cho et al., "Synthesis of ZSM-5 Films and Monoliths with Bimodal Micro/Mesoscopic Structures" Advanced Functional Materials, 2004, vol. 14, No. 1, pp. 49-54.
Corma, "Inorganic Solid Acids and Their Use in Acid-Catalyzed Hydrocarbon Reactions" Chemical Reviews, 1995, vol. 95, pp. 559-614.
Corma et al., "High-throughput synthesis and catalytic properties of a molecular sieve with 18- and 10-member rings" Nature, 2006, vol. 443, pp. 842-845.
Christensen et al., "Crystals in Crystals-Nanocrystals within Mesoporous Zeolite Single Crystals", J. Am. Chem. Soc., 2005, 127, 8098-8102.
Davis et al., "A Molecular Sieve with Eighteen-membered Rings" 1988, vol. 331, pp. 698-699.
Davis, "Ordered Porous Materials for Emerging Applications" Nature, 2002, vol. 417, pp. 813- 821.
Freyhardt et al., "A High-Silica Zeolite with a 14-tetrahedral-atom Pore Opening" Nature, 1996, vol. 381, pp. 1-4.
Holm et al., "Catalysis with hierarchical zeolites" Catalysis Today, 2011, vol. 168, pp. 3-16.
Kärger et al., "Mass Transfer in Micro- and Mesoporous Materials" Chem. Eng. Technol., 2002, vol. 25, pp. 769-778.
Kresge et al., "Ordered Mesoporous Molecular Sieves Synthesized by a Liquid-Crystal Template Mechanism" Letters to Nature, 1992, vol. 359, pp. 710-712.
Liu et al., "Aluminosilicate mesostructures with improved acidity and hydrothermal stability" Journal of Materials Chemistry, 2002, vol. 12, pp. 3179-3190.
Na et al., "Recent advances in the synthesis of hierarchically nanoporous zeolites" Microporous and Mesoporous Materials, 2013, vol. 166, pp. 3-19.
Prokesova et al., "Preparation of nanosized micro/mesoporous composites" Materials Science and Engineering C, 2003, vol. 23, pp. 1001-1005.
Shetti et al., "Assessment of the mesopore wall catalytic activities of Mfi zeolite with mesoporous/ microporous hierarchical structures" Journal of Catalysis, 2008, vol. 254, pp. 296-303.
Strohmaier et al., "Structure of the First Silicate Molecular Sieve with 18-Ring Pore Openings, Ecr-34" Journal of American Chemical Society, 2003, vol. 125, pp. 16035-16039.
Thibault-Starzyk et al., "Quantification of enhanced acid site accessibility in hierarchical zeolites — the accessibility index" Journal of Catalysis, 2009, vol. 264, pp. 11-14.
Wagner et al., "Cit-5: a high-silica zeolite with 14-ring pores" Chemical Communications, 1997, Issue 22, pp. 2179-2180.

\* cited by examiner

METHOD OF PRODUCING ZEOLITE ENCAPSULATED NANOPARTICLES

CROSS REFERENCE TO RELATED APPLICATIONS

This application is a U.S. National Phase Application of PCT International Application Number PCT/EP2014/064428, filed on Jul. 7, 2014, designating the United States of America and published in the English language, which is an International Application of and claims the benefit of priority to European Patent Application No. 13175324.6, filed on Jul. 5, 2013. The disclosures of the above-referenced applications are hereby expressly incorporated by reference in their entireties.

FIELD OF THE INVENTION

The invention concerns a method for making zeolite or zeotype encapsulated metal nanoparticles and zeolite or zeotype encapsulated metal nanoparticles produced by the method.

BACKGROUND OF THE INVENTION

In the view of the current environmental challenges there is an urgent need to develop a more sustainable chemical industry through more efficient chemical transformations and by developing new highly selective and cost-effective catalysts. One approach towards enhanced catalytic performance of supported metal catalysts is to increase the active metal surface by synthesizing small metal nanoparticles (often <10 nm in diameter). However, small nanoparticles are often prone to sintering which decreases the catalytic activity over time. The development of sinter-stable heterogeneous nano particle catalysts is therefore of great importance.

Zeolites are crystalline alumina silicate materials that exhibit a highly ordered porous structure with pores of molecular diameter. IUPAC identifies this type of porosity as microporous, as the size of the pores are not wider than 2 nm. The other groups of porosity are mesoporous (pore size between 2-50 nm) and macroporous (pore size larger than 50 nm). Zeolites consist of tetrahedral $TO_4$ units (T=Si or Al), which gives the framework an overall composition of $TO_2$. These materials have a clear organized framework throughout the crystals, giving rise to highly ordered pores and a large internal surface area. By replacing a silicon atom with an aluminium atom, it is possible to generate a deficit of charge, which is compensated by a cation located nearby. The cation is usually an alkali metal (such as sodium), alkali earth metal, or possibly a $H^+$ ion. If the cation is a proton, the zeolite becomes a strong Brønsted acid. All these characteristics give rise to a lot of uses for zeolites.

Today, nearly 60 different natural occurring zeolites are known, while 201 can be prepared synthetically [1]. These zeolites have different structures, due to different Si—O—Al linkages, and a different number of Si or Al atoms linked in each "cage". This also creates different pore system of one-, two-, or three-dimensions in the zeolite.

As the pores are very regular, and around the same size in diameter as molecules, it is possible for zeolites to function as molecular sieves. Due to their chemical structure and molecular sieve properties, zeolite catalysts exhibit high selectivity for a variety of chemical reactions. Since most of the surface area and the active sites are within the zeolite, the shape of the pores and channels give rise to shape selective catalysis. Commonly there is distinguished between three types of molecular sieving effects:

1) Reactant shape selectivity: Only molecules small enough can enter the zeolite pores and undergo chemical transformation or be adsorbed.
2) Product shape selectivity: The size of the pores is too small, that not all possible products can diffuse out of the zeolite after reaction. This leads to an increased selectivity towards smaller molecules or isomers.
3) Restricted transition-state shape selectivity: Here the formation of too large transition state intermediates are prevented due to zeolite pore size. FIG. 1 illustrates the three different kinds of shape selectivity.

Zeolite Synthesis

In general, zeolite synthesis is a crystallization process, where silica and alumina species dissolve and react to give a less soluble crystalline alumina/silicate product. The crystallization process is typically performed in a hydrothermal process where the zeolite precursors is put in an autoclave and heated to relatively high temperatures and autogenous pressures. The high pressure is due to the evaporation of water inside the autoclave, and is very important for the synthesis. In a typical synthesis the zeolite precursors is dissolved or suspended in an aqueous solution of a structure directing agent (SDA) and an alkali hydroxide to catalyze the breaking and formation of chemical bonds [4].

The structure directing agents are almost always organic amine cations. Some of the most commonly used organic structure directing agents are tetramethyl-ammonium (TMA), tetraethylammonium (TEA), and tetrapropylammonium (TPA), though compounds as diverse as Choline, 1,6-diaminohexane, and hexanediol have been used. During the zeolite crystallization process, the zeolites form around molecules of the structure directing agent. The shape and properties of the structure directing agent causes the zeolites forming around it to take a certain shape. Stoichiometric analysis of samples of ZSM-5 has indicated that one $TPA^+$ molecule occupies each intersection between pores in the zeolite [2].

For sources of silicon, mostly sodium silicate, fumed silica or tetraethoxy ortho-silicate is used, while sodium aluminate, aluminum nitrate or -chloride are typical sources of aluminum [3]. The mixture of zeolite precursors or zeolite gel is then transferred to an autoclave and heated to a predetermined temperature, often between 120-200° C. Within days, possible weeks, the precursors begin to crystallize and form the zeolite. After the synthesis, the autoclave is cooled to room temperature, and the zeolite material is washed with water and isolated by filtration or centrifugation. The zeolite is then calcined at around 500-600° C. to remove residual SDA and framework water. At last the zeolite can be ion exchanged. This can either be done to introduce hydrons, alkali metal, alkali earth metal, lanthanoid or transition metal cations.

One method to produce a porous system inside a zeolite is templating. Several types of templates have been utilised for the introduction of pores in zeolites. One of them; hard templating applies a solid material to generate a porous system in addition to the inherent micropores. This method has proved to be very effective and a highly versatile approach. Templates include organic aerogels, polymers, and carbon in different forms. Here, only carbon will be discussed. One of the well-known methods is the crystallization of zeolite gel in porous carbon particles. If the amount of synthesis gel relative to the carbon template is sufficient, the zeolite crystals continue to grow after nucleation in the cavities of the carbon. This will allow the zeolite crystal to encapsulate the carbon. Combustion of the carbon particles embedded in the zeolite crystal, will lead to the formation of mesopores [37]. Several types of carbon nanoparticles have been used [38], including carbon nanotubes [39] and nanofibers.

In 1983 Taramasso et al. incorporated titanium ions into silicalite-1 (denominated as TS-1) [56]. The incorporation of titanium, is a isomorphous substitution in the MFI lattice of the silicalite-1. The presence of a titanium atom gave rise to different catalytic properties, than the selective acid catalytic properties displayed by conventional alumina silicate zeolites. The TS-1 has been found useful in selective oxidation reactions, such as the hydroxylation of phenols, epoxidation of alkenes, and ammoxidation of ketones [57-61].

Encapsulation of metal nanoparticles in a zeolite structure can improve the physical properties of the zeolite, but in addition to that; the encapsulated metal nanoparticles can have catalytically properties themselves. As a further potential advantage, the encapsulation can protect the individual nanoparticles from contact with other nanoparticles, thereby preventing sintering of the nanoparticles when these are subjected to elevated temperatures.

In spite of the great technological, environmental and economic interests, general methods for the stabilization of metal nanoparticles against sintering are far from being fully developed, although for some specific systems it has been achieved by optimizing the interaction of nanoparticles with a support material or by encapsulation of the metal particles [52, 93, 94]. However, these known catalytic systems are in general very expensive and difficult to synthesize and they cannot be produced in industrial scale. Nanoparticles encapsulated in zeolite-like structure have only been reported in a handful of papers [46, 52, 95-99].

The encapsulation of nanoparticles is an area of increasing interest. This is a possible solution to the widely known problem of deactivation due to sintering. Several methods have been developed to produce sinter-stable nanoparticle catalyst, including encapsulating in mesoporous silica matrix or by using a protective shell [45-48]. None of these materials are however shape-selective. By encapsulating metal nanoparticles in a zeolite matrix, on the other hand, shape selective catalysis is possible. In addition, the thermal stability of zeolites and high surface area, makes zeolites particularly useful for this application. Post treatment deposition of nanoparticles inside zeolites has been reported in literature [49-51]. A limitation of these methods is however that they require zeolites containing cages.

By post-synthesis treatments the nanoparticles are in the cages and/or in the pores of the zeolite and it can be difficult to control the size and location of the nanoparticles. Both Laursen et al. and Tøjholt et al. have successfully synthesised a MFI zeolite containing gold nanoparticles (size 1-3 nm), which showed to be highly stably versus sintering [52, 53]. In addition, the gold nanoparticles were only accessible through the micropores of the zeolite. The synthesis is however difficult, and requires a lot of exotic materials and time.

So, despite the growing demand, a fast, efficient and economically process for manufacturing zeolite or zeotype encapsulated metal nanoparticles which are sinter-resistant that can be scaled up for industrial application has not yet been reported.

SUMMARY OF THE INVENTION

The present invention relates to method for producing zeolite, zeolite-like or zeotype encapsulated metal nanoparticles, the method comprises the steps of:

1) Adding one or more metal precursors to a silica or alumina source;
2) Reducing the one or more metal precursors to form metal nanoparticles on the surface of the silica or alumina source;
3) Passing a gaseous hydrocarbon, alkyl alcohol or alkyl ether over the silica or alumina supported metal nanoparticles to form a carbon template coated zeolite, zeolite-like or zeotype precursor composition;
4a) Adding a structure directing agent to the carbon template coated zeolite, zeolite-like or zeotype precursor composition thereby creating a zeolite, zeolite-like or zeotype gel composition;
4b) Crystallising the zeolite, zeolite-like or zeotype gel composition by subjecting said composition to a hydrothermal treatment;
5) Removing the carbon template and structure directing agent and isolating the resulting zeolite, zeolite-like or zeotype encapsulated metal nanoparticles.

The present invention also relates to a zeolite, zeolite-like or zeotype encapsulated metal nanoparticles manufactured by the method according to the present invention.

FIGURES

FIG. 1: The three types of shape selectivity [3].

Figure 2A:
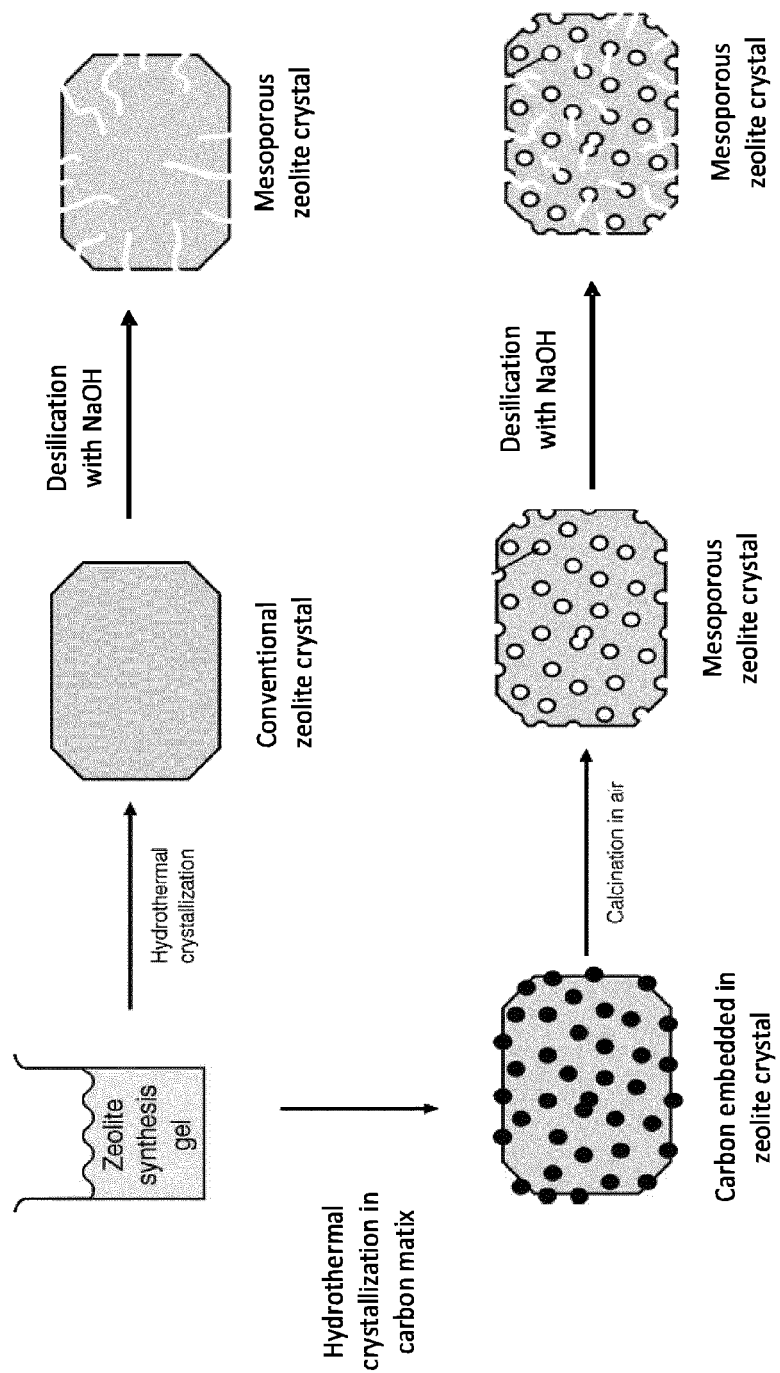

FIG. 2a: Overview of principles of zeolite synthesis.

Figure 2B:
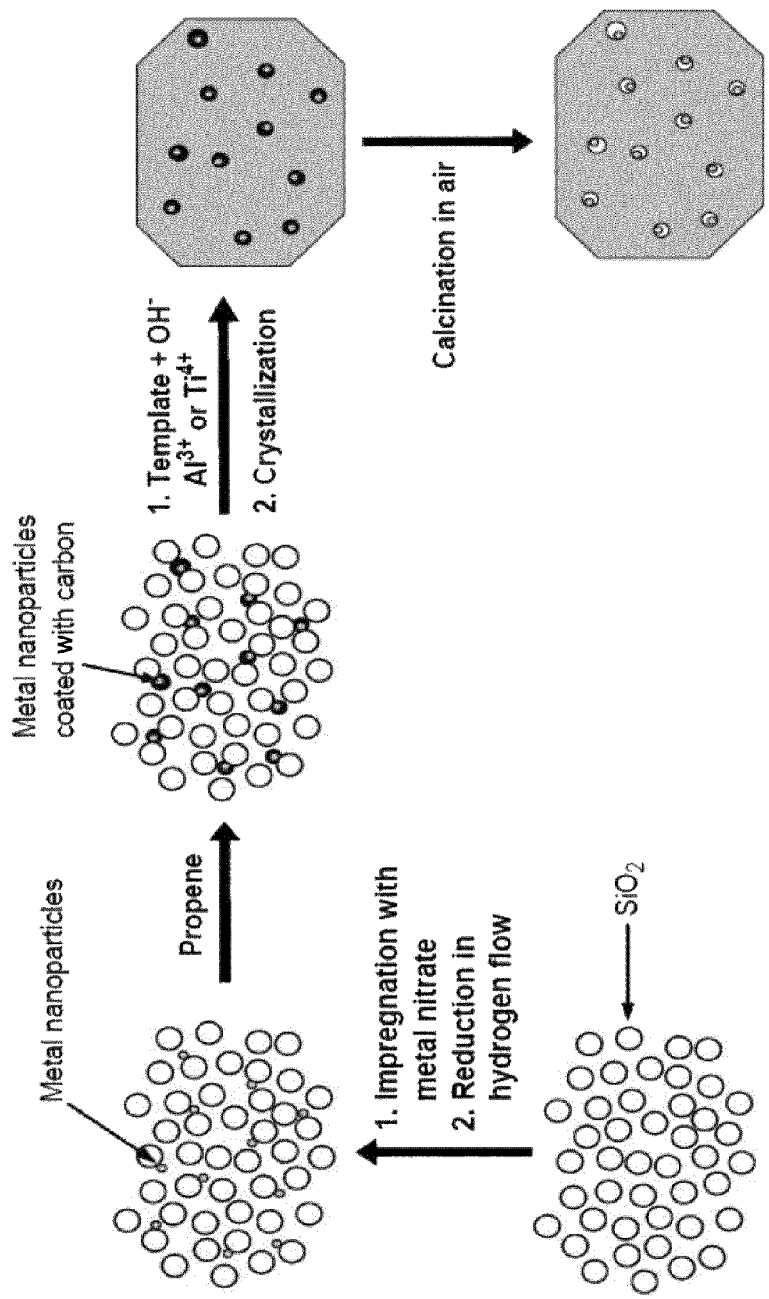

FIG. 2b: Overview of developed procedure for the synthesis of carbon template mesoporous zeolites and sintering stable heterogeneous nanoparticle catalysts.

Figure 3:
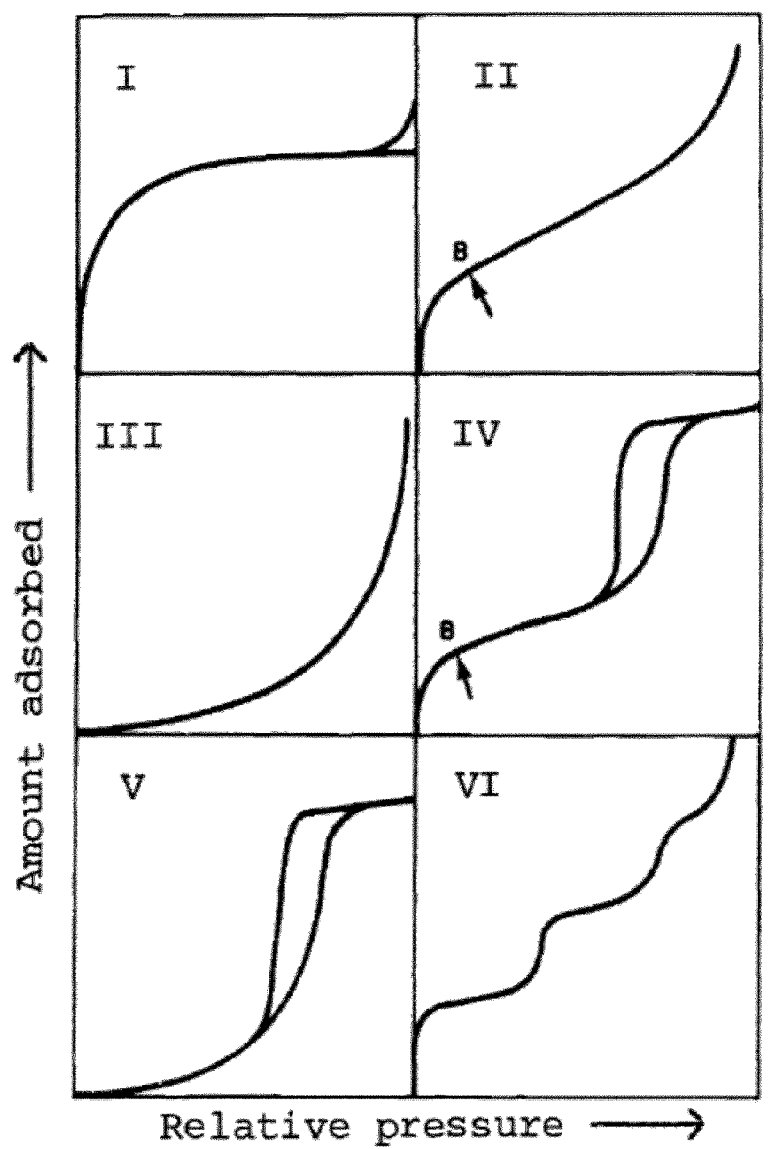

FIG. 3: The six types of isotherms as classified by IUPAC [80].

Figure 4:
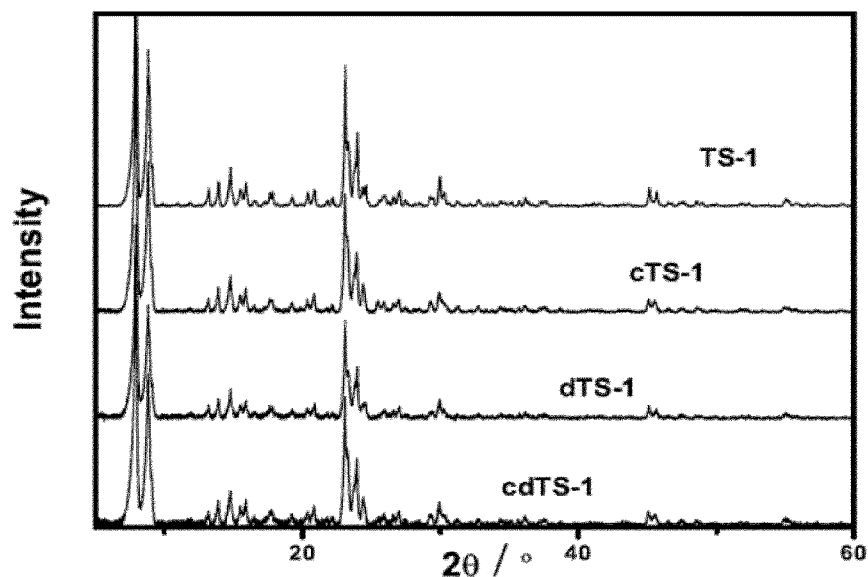

FIG. 4: XRPD patterns of conventional (TS-1), carbon-templated (cTS-1), desilicated (dTS-1), and TS-1 subjected to both carbon-templating and desilication (cdTS-1).

Figure 5:
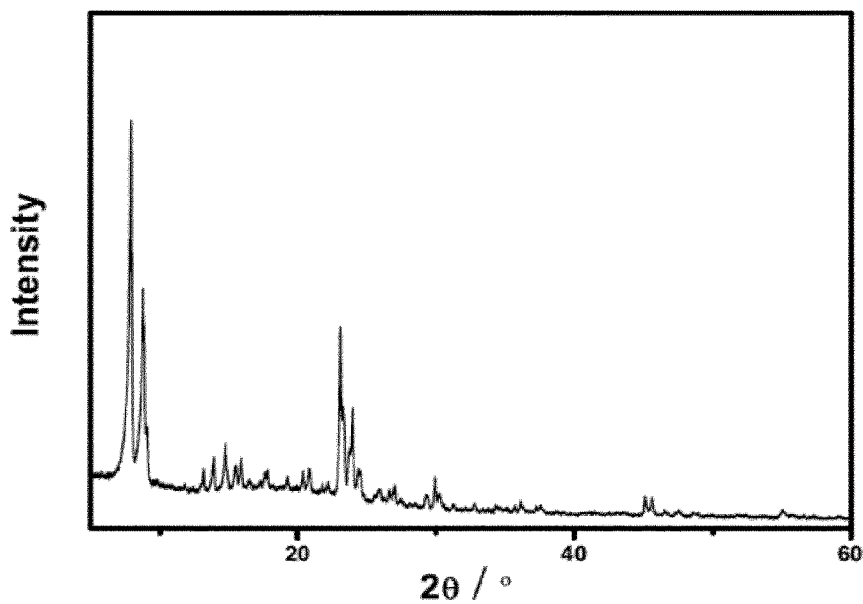

FIG. 5: XRPD pattern of Ni-0.74-TS-1 synthesized using propene.

Figure 6:
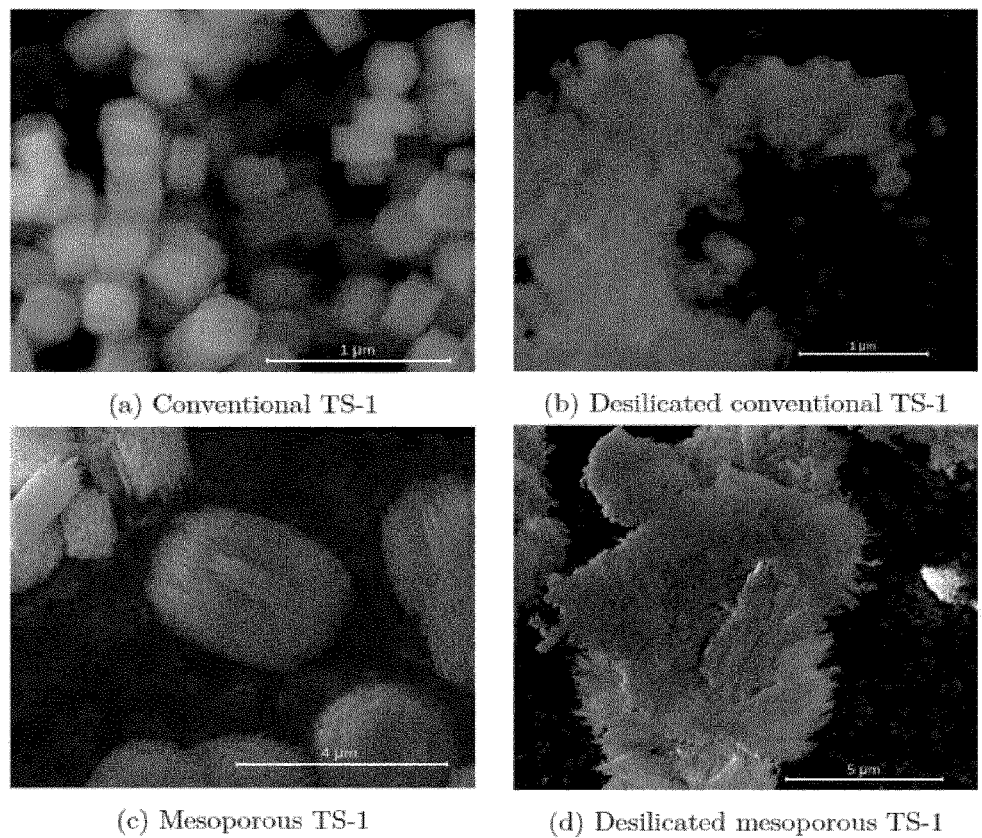

FIG. 6: Scanning electron microscope images of conventional and mesoporous TS-1, plus their desilicated counterparts.

Figure 7:
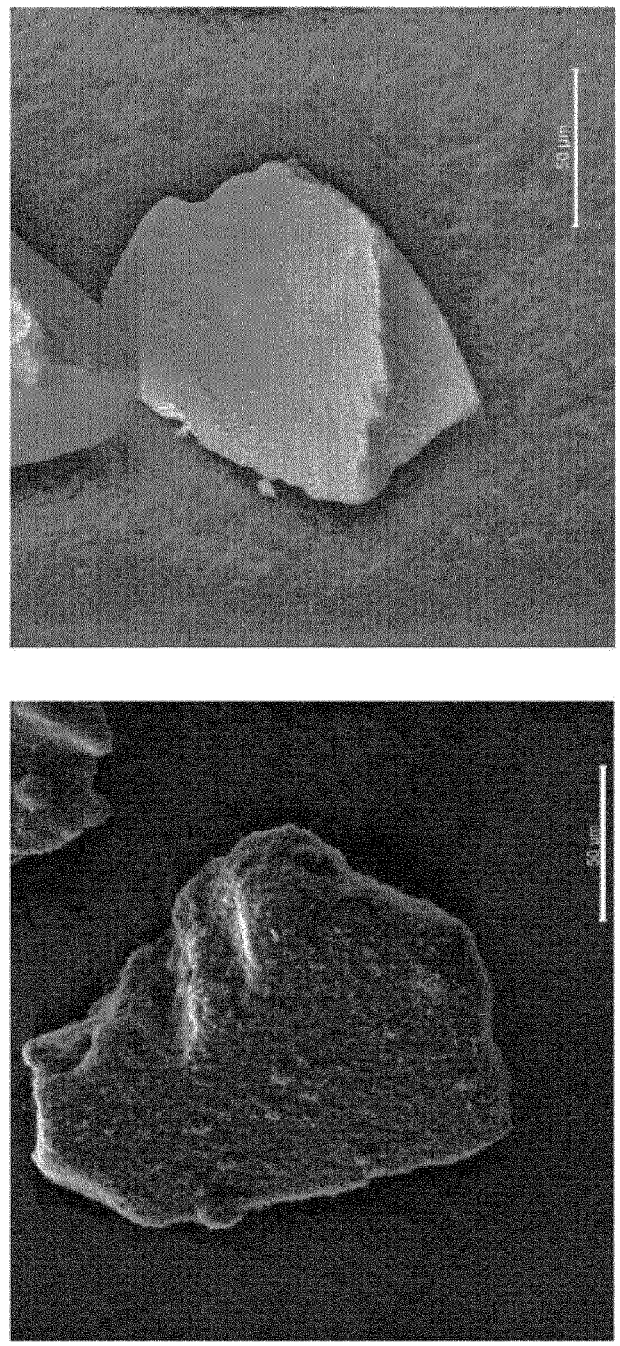

FIG. 7: Scanning electron microscope images of silica samples prepared by coking of nickel and iron nanoparticles.

Figure 8:
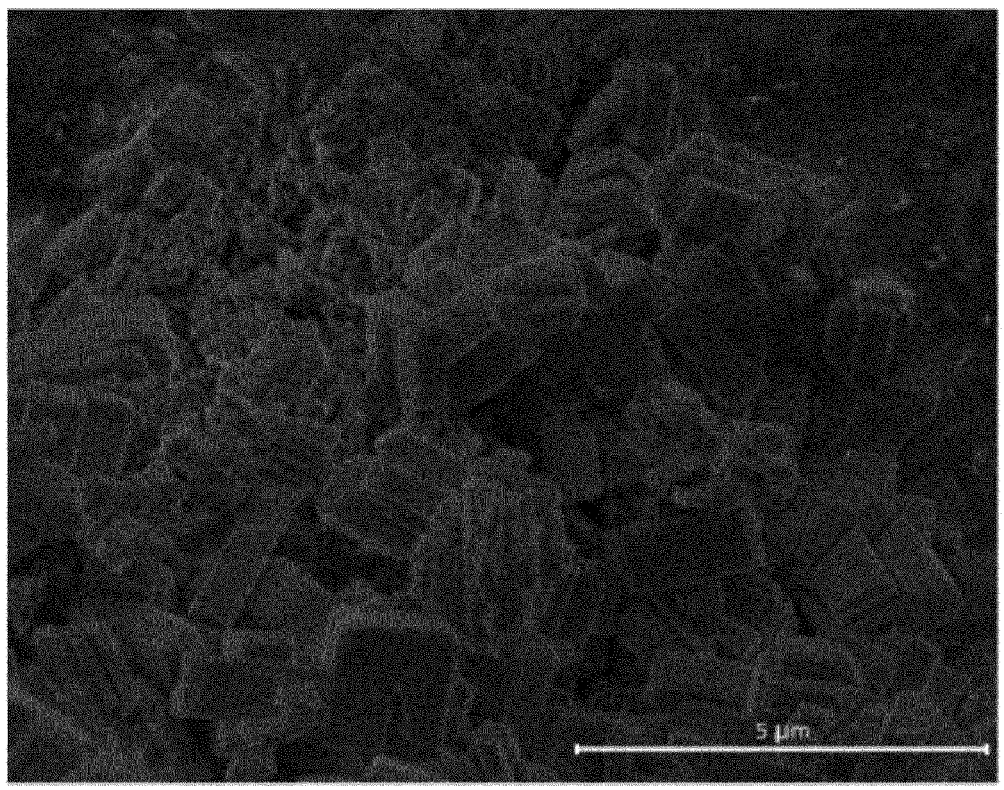

FIG. 8: Scanning electron microscope images of TS-1 prepared with nickel nanoparticles.

Figure 9:
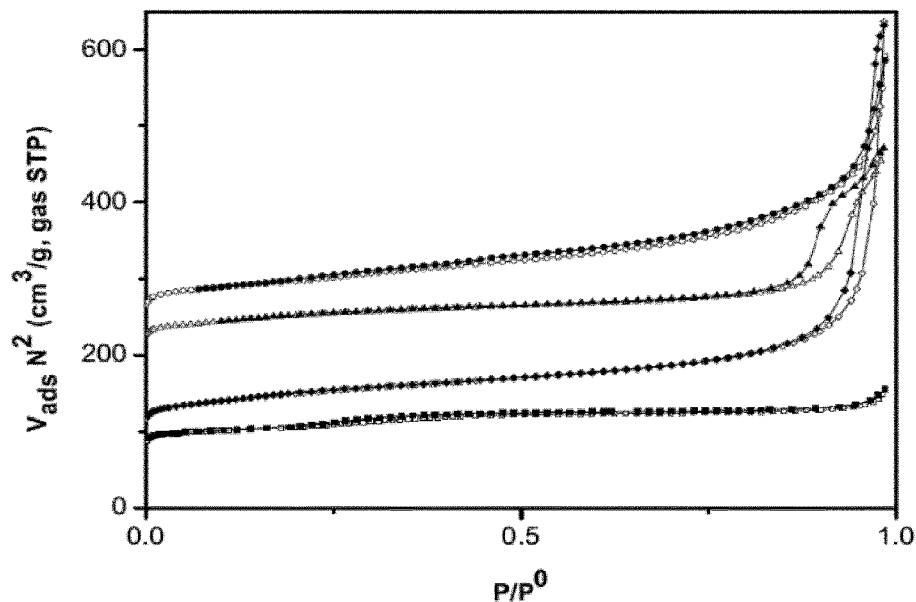

FIG. 9: Nitrogen adsorption/desorption isotherms of conventional and mesoporous samples. (□) TS-1, (○) dTS-1, (◇) cTS-1, (Δ) cdTS-1. Blank symbols represent the adsorption isotherm, while filled represent the desorption. (please note the offset).

Figure 10:
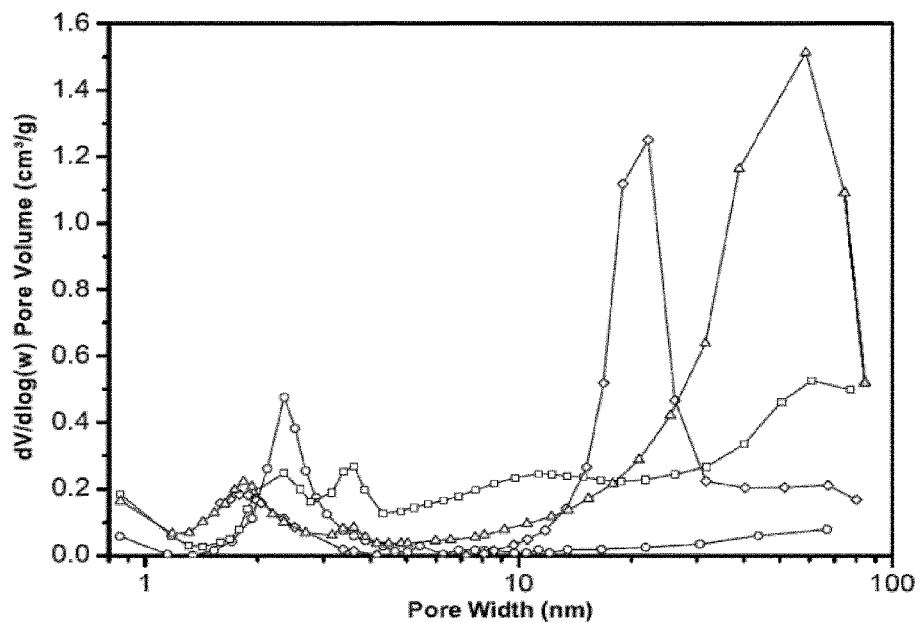

FIG. 10: BJH pore size distribution based on the desorption isotherms. (□) TS-1, (○) dTS-1, (◇) cTS-1, (Δ) cdTS-1.

Figure 11:
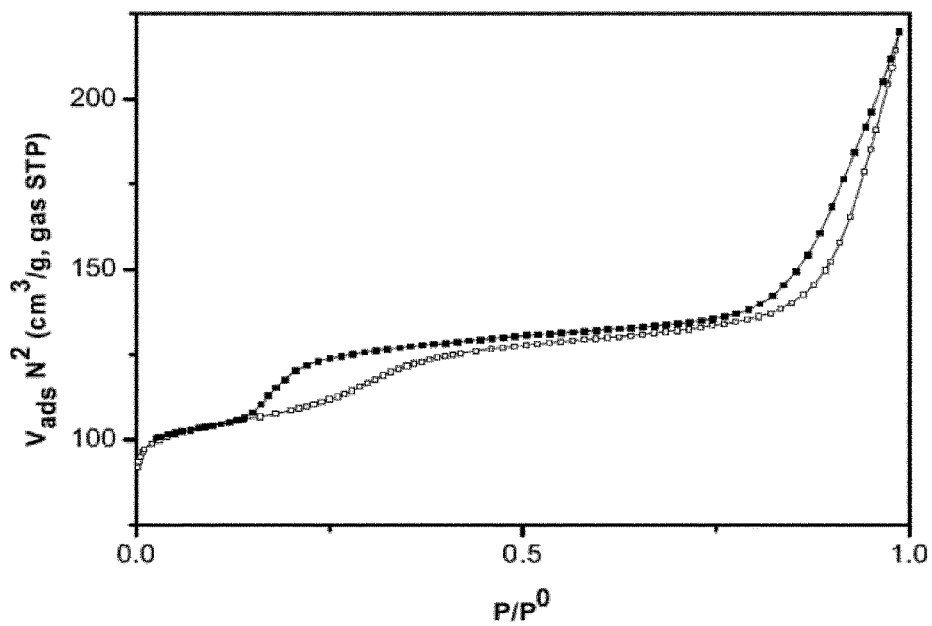

FIG. 11: Nitrogen adsorption/desorption isotherms of Ni-0.74-TS-1.

Figure 12:
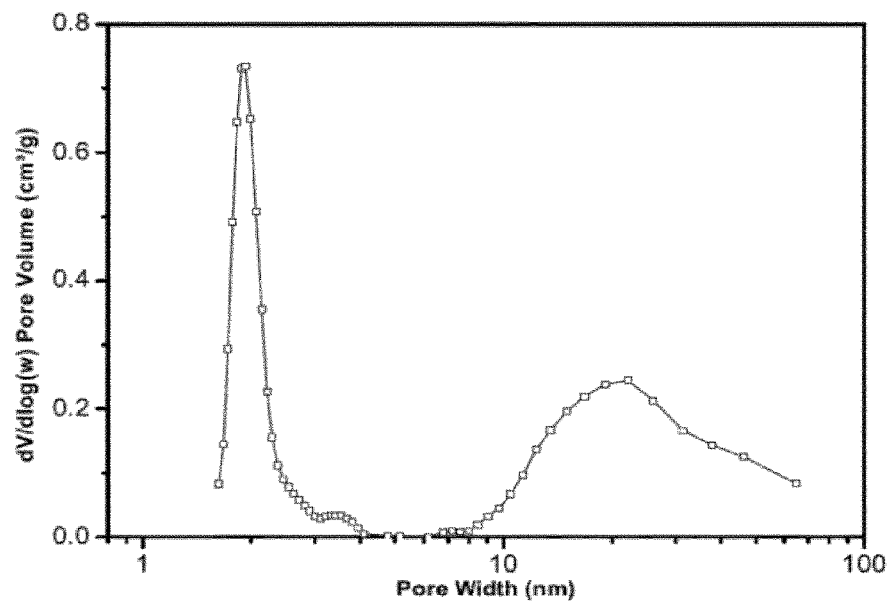

FIG. 12: BJH pore size distribution of Ni-0.74-TS-1 based on the desorption isotherms.

Figure 13:
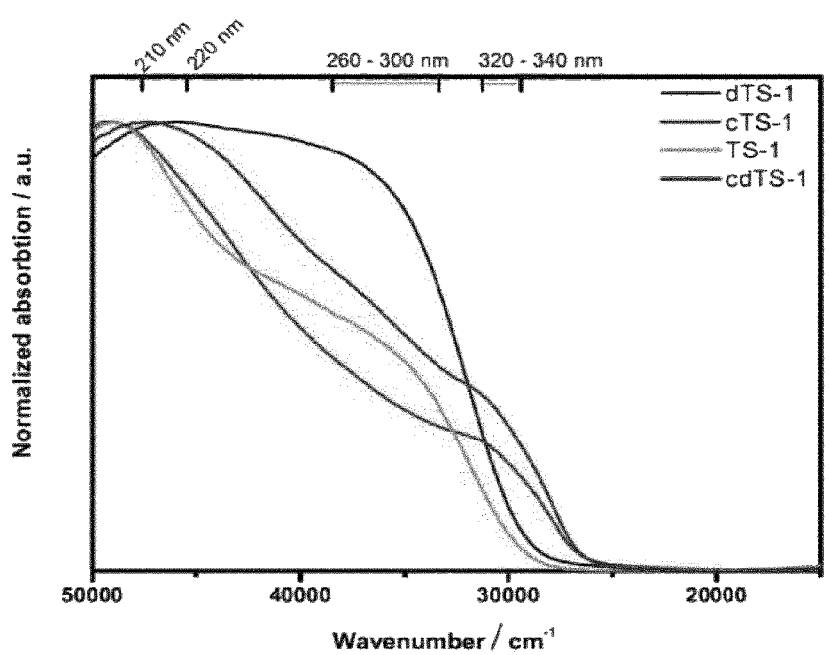

FIG. 13: UV-Vis spectra of TS-1 and its mesoporous derivates.

Figure 14:
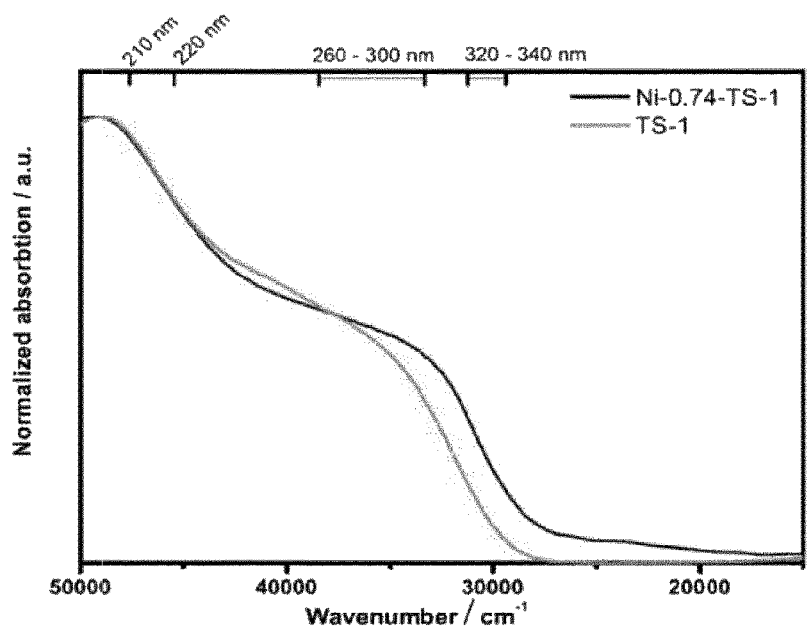

FIG. 14: UV-Vis spectra of Ni-0.74-TS-1 and conventional TS-1.

Figure 15:
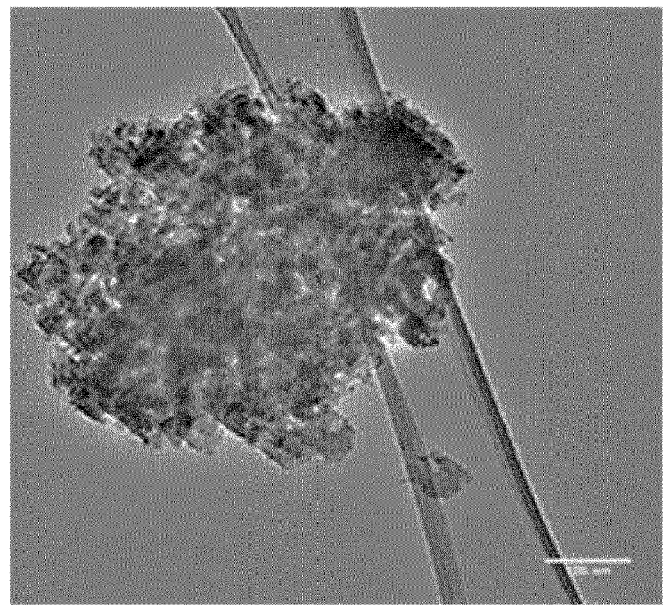

FIG. 15: Transmission electron microscopy of a mesoporous MFI zeolite synthesized using methane, where the material is heated to 550° C. under argon before methane gas is added.

Figure 16:
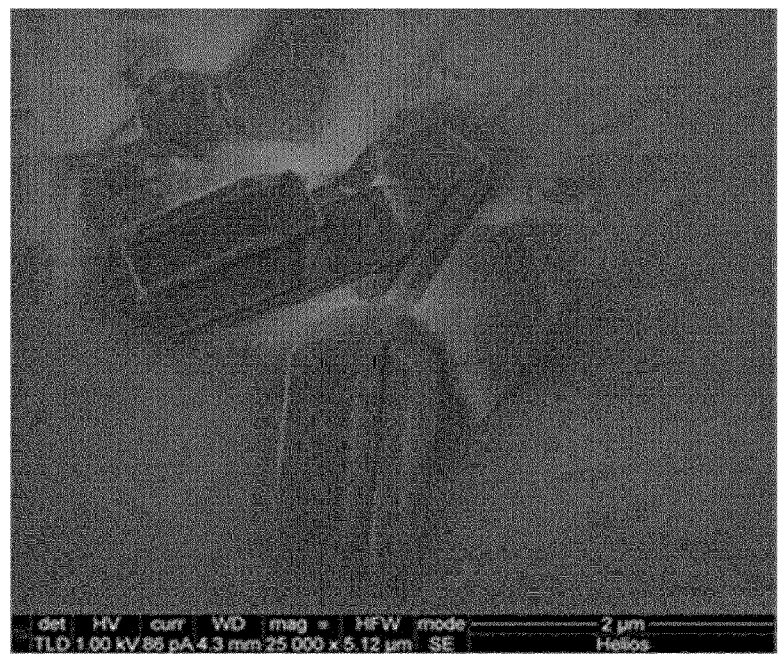

FIG. 16: Scanning electron microscope images of a MFI zeolite synthesized using methane, where the material is heated to 700° C. under argon before methane gas is added.

Figure 17A:
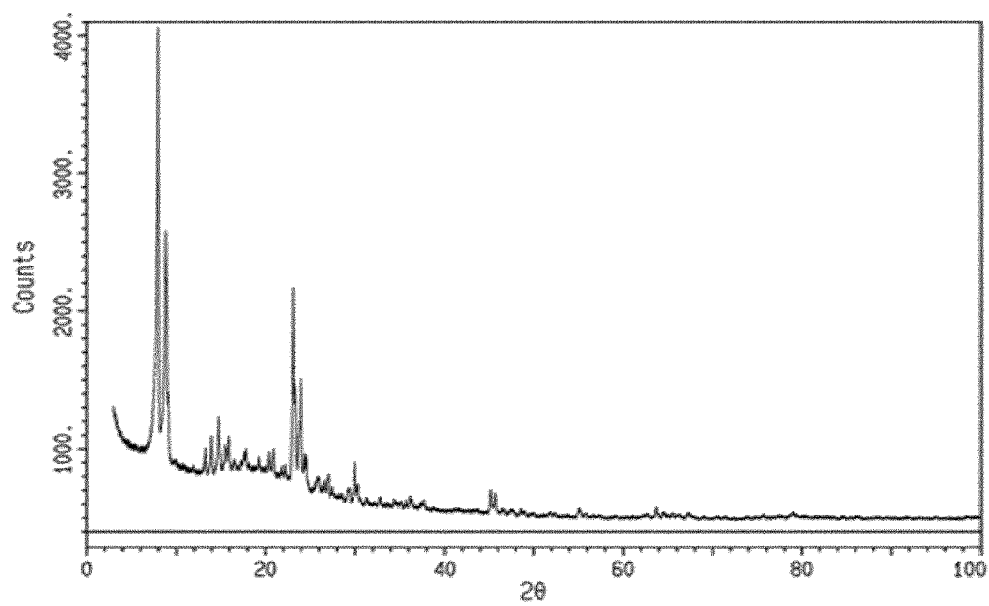
Figure 17B:
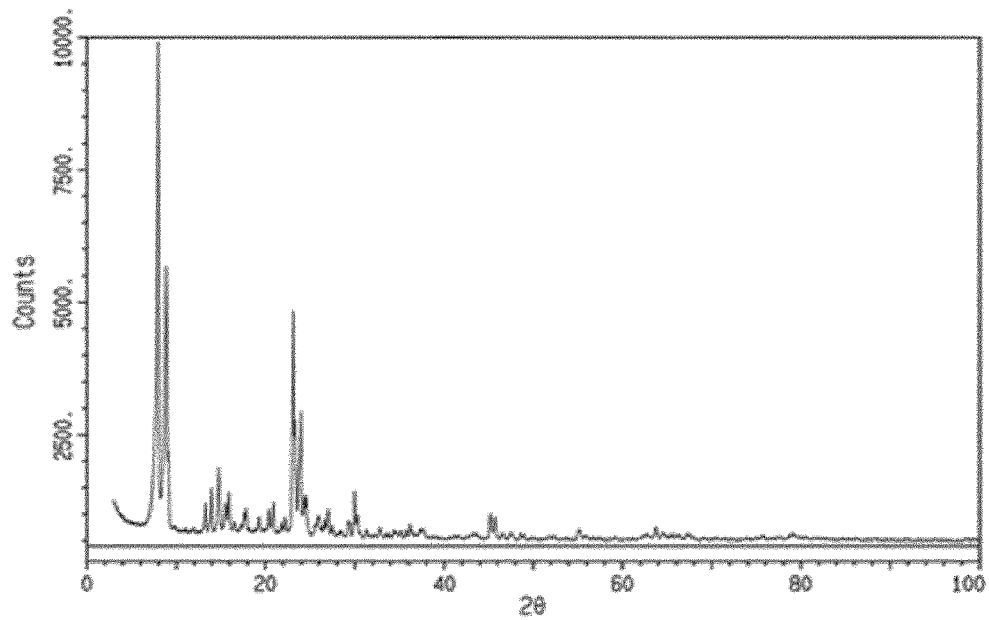

FIGS. 17*a-b*: XRPD pattern of MFI synthesized using methane, where FIG. 17*a* represents a synthesis method, where the material is heated to 550° C. under argon before methane gas is added and FIG. 17*b* represents a synthesis method, where the material is heated to 700° C. under argon before methane gas is added.

DETAILED DESCRIPTION OF THE INVENTION

In the following detailed description of the invention, reference is made to the examples, including tables and figures.

In this application a method for producing zeolite, zeolite-like or zeotype encapsulated metal nanoparticles is presented. This is a new method to synthesize zeolite, zeolite-like or zeotype encapsulated metal nanoparticles where the carbon template is generated by a direct coking process facilitated by pre-formed metal nanoparticles on the silica/aluminium source.

The invention therefore relates to a method for producing zeolite, zeolite-like or zeotype encapsulated metal nanoparticles, the method comprises the steps of:
1) Adding one or more metal precursors to a silica or alumina source;
2) Reducing the one or more metal precursors to form metal nanoparticles on the surface of the silica or alumina source;
3) Passing a gaseous hydrocarbon, alkyl alcohol or alkyl ether over the silica or alumina supported metal nanoparticles to form a carbon template coated zeolite, zeolite-like or zeotype precursor composition;
4a) Adding a structure directing agent to the carbon template coated zeolite, zeolite-like or zeotype precursor composition thereby creating a zeolite, zeolite-like or zeotype gel composition;
4b) Crystallising the zeolite, zeolite-like or zeotype gel composition by subjecting said composition to a hydrothermal treatment;
5) Removing the carbon template and structure directing agent and isolating the resulting zeolite, zeolite-like or zeotype encapsulated metal nanoparticles.

The metal nanoparticles are still present within each single crystal of the zeolite after synthesis. When the carbon template has been removed by calcinations from the zeolite structure the nanoparticles are individually encapsulated within the created pores or cavities of the zeolite structure, so that the individual nanoparticles are protected from contact with other nanoparticles, thereby preventing sintering of the nanoparticles when these are subjected to elevated temperatures.

The zeolite, zeolite-like or zeotype encapsulated metal nanoparticles are preferably sinter stable or sinter resistant.

By encapsulating metal nanoparticles in a zeolite matrix, shape selective catalysis is possible.

By encapsulation, the metal nanoparticles are immobilised and sustained in the entire zeolite crystals, and thus more stable towards sintering. The nanoparticles are accessible through the framework of pores which act as molecular sieves.

The novel method can be used to synthesize sintering stable heterogeneous nanoparticle catalysts useful for environmental protection and production of chemicals. The zeolite-based catalysts containing metal nanoparticles are synthesized according to the approach depicted in FIG. 2*b*. The hydrocarbon gas alkyl alcohol or alkyl ether which is employed in step 3 decomposes on the metal surface to leave a protective layer of carbon around the metal nanoparticles. It is expected that this novel synthesis method can improve the current synthesis of encapsulated metal nanoparticles in zeolites.

The encapsulation of metal nanoparticles within the zeolite structure inhibits sintering, thereby preserving their high surface area required for the effective catalytic activity. This novel approach for preparation of sintering stable heterogeneous nanoparticle catalysts is rather simple and can be used to develop novel automotive exhaust catalyst. Moreover, it is also the more general method for the stabilization of metal nanoparticles against sintering which could find use in the chemical and pharmaceutical industry. For example, the heterogeneous gold, silver and platinum nanoparticle catalysts are active and selective catalysts for several oxidation reactions.

The method of the invention is based on carbon templating and originates from the desire to develop a fast, efficient and cheap alternative method that can be scaled up for industrial application more easily than the known sucrose method [41]. An overview of this synthesis is presented in FIG. 2*b*.

Different zeolite structures (framework) are suitable for the above method of production. The zeolite structure can be zeolite beta (BEA), Y (FAU), ZSM-5 (MFI), ZSM-11 (MEL) or ZSM-12 (MTW).

Throughout the description, when zeolites are mentioned this is meant to comprise zeolites, zeolite-like materials and zeotypes unless otherwise specifically mentioned.

By the term zeolite-like is meant non-silicon comprising material. Examples of zeolite-like materials are non-silicon comprising materials such as aluminium phosphate (AlPO4) molecular sieves, known as AlPO's. The phosphorous compound can be selected from the group consisting of phosphoric acid, phosphate salts and mixtures thereof. By the term "phosphate salts" is meant salts of phosphates, monohydrogen phosphates and dihydrogen phosphates.

By zeolite, zeolite-like and zeotype particle is meant zeolite, zeolite-like and zeotype crystal or zeolite, zeolite-like and zeotype material.

"Metal nanoparticles" also comprises mixtures of metals nanoparticles.

By metal nanoparticles is also meant metal oxide nanoparticles and metal nitrate nanoparticles. The metal or mixture of metal precursors might form into the respective oxides or nitrates. This can happen either during the manufacturing process or in the end product.

Possible silica sources for zeolites may be bulk silica of different quality and alumina contamination, including pure silica, fumed silica, sodium silicate or other soluble silicate salts, precipitated silica, tetraethyl orthosilicate and other alkoxy-silicates, silicic acid, etc.

Possible aluminium sources for zeolites may be aluminum nitrate, aluminum sulphate, aluminum phosphate, sodium aluminate ect.

The inherent micropores in the zeolite structure are also here called primary porosity whereas the ekstra pores created by the method of the present invention are referred to as secondary porosity. This secondary porosity can both be micropores or mesopores.

The first step in the process is to add a metal or a mixture of metal precursors to a silica/alumina precursor. In one embodiment the first step is performed at elevated temperatures such as from 50° C. to 150° C., such as around 80° C.

The metal precursors can be added by grinding, impregnation, co-precipitation, deposition-precipitation or chemical vapor deposition.

Impregnation: a solution, e.g. an aqueous or alcoholic solution of one or several transition metal precursors is applied to a silica/alumina source. The solution is dryed, e.g. in an oven at 80° C. overnight, whereby water is evaporated and left is the metal on the surface of the silica/alumina source.

Deposition Precipitation: silica and the metal or mixture of metals is mixed together in a solution. By changing pH or adding chemicals, e.g. $H_2O_2$, the character of the metal change to another compound and deposit on the silica.

Chemical Vapour Deposition: The metal or mixture of metals can be in a gas phase or liquid phase. If the metal is in a liquid phase the liquid is heated to the boiling point and lead over the silica where it is deposited. If the metal is in the gas phase, the gas is lead over the silica where it is deposited.

In one embodiment nickelparticles are made volatile by CO and carbonyl compound are created, which are deposited on the silica and creates carbon nanotubes.

In one embodiment of the method for producing zeolite, zeolite-like or zeotype encapsulated metal nanoparticles the one or more metal(s) is selected from the group consisting of group 4 elements, group 6 elements, group 7 elements, group 8 elements, group 9 elements, group 10 elements, group 11 elements or group 12 elements or mixtures thereof. The group elements are defined by the new IUPAC numbering.

In one embodiment of the method the one or more metal(s) is selected from the group consisting of titanium, osmium, iridium, platinum, ruthenium, palladium, rhodium, rhenium, copper, nickel, iron, cobalt, silver, gold, cadmium, molybdenium or mixtures thereof. In one embodiment the metal is nickel.

In one embodiment of the method for producing zeolite, zeolite-like or zeotype encapsulated metal nanoparticles the first step is performed in a liquid phase, e.g. in an aqueous or alcoholic solution, in a gas phase or in a solid phase. The aqueous or alcoholic solution of of the one or more metal precursors could comprise nitrates, carbonates, acetates sulphates orchlorides.

In another embodiment, the first step in the process involves impregnating a silica or alumina precursor with an aqueous or alcoholic solution of one or more transition metal precursors. The possible metals especially include Fe, Co, Ni, Cu, Ru, Rh, Pd, Ag, Pt, Au, Mo, and mixtures thereof. The possible metal precursor could be nitrates, carbonates, acetates, sulfates, chlorides, carbonyls, and several other cheap and readily available chemicals.

The possible metal can also be a metal alloy such as gold-platinum, copper-palladium, ruthenium-copper, platinum-iridium, platinum-palladium, platinum-ruthenium, cobalt-molybdenum, nickel-molybdenum, or palladium-gold, where one of the metals in the metal alloy can be present in an amount of from 1 to 50%. The optimal weight ratio between the metals in the alloy depends on the metal alloy.

The second step in the process involves reducing the one or more metal precursors to form metal nanoparticles on the surface of the silica or alumina source. The metal precursors is reduced in a reducing atmosphere, for instance in a stream of hydrogen gas, or decomposed by a thermal treatment to give the corresponding transition metal nanoparticles. The transition metal nanoparticles can also be in the form of metal oxide nanoparticles or metal nitrate nanoparticles. This reduction step is in one embodiment performed at elevated temperatures, e.g. from 200 to 800° C. such as from 200 to 700° C., or such as from 200 to 600° C.

The third step in the process involves passing a gaseous hydrocarbon, alkyl alcohol or alkyl ether over the silica or alumina source with the impregnated metal nanoparticles, forming a zeolite precursor composition comprising carbon coated metal nanoparticles. The physical shape of the carbon (also called the carbon template) coating the nanoparticles can vary depending on the process conditions. In one embodiment the carbon is in the form of whiskers (nanotubes). In another embodiment the carbon is in the form of nanofibers. In another embodiment the carbon is in the form of spheres encircling the metal nanoparticles.

In one embodiment the flow of gaseous hydrocarbon, alkyl alcohol or alkyl ether is in the range of 20 to 500 ml/min, 20 to 400 ml/min, 100 to 400 ml/min, 30 to 100 ml/min, 50 to 90 ml/min, 50 to 70 ml/min or 60 to 70 ml/min.

In one embodiment, the third step of the process involves heating the silica or alumina and metal nanoparticles to 200-1100° C., such as from 200-800° C. or from 300-1100° C.

In separate embodiments the hydrocarbon is selected from aliphatic hydrocarbons having 1 to 8 carbon atoms, having 1 to 3 carbon atoms, alkenes having 2 to 6 carbon atoms, aromatic hydrocarbons having 6 to 10 carbon atoms and cyclic hydrocarbons having 3 to 8 carbon atoms.

In one embodiment the hydrocarbon gas is selected from methane, propene, xylene, methane or benzene.

In other separate embodiments the alkyl alcohol is selected from aliphatic alcohols having 1 to 8 carbon atoms, or having 1 to 3 carbon atoms.

In other separate embodiments the alkyl ether is selected from aliphatic ethers having 2 to 8 carbon atoms, or having 2 to 4 carbon atoms.

In a specific embodiment the alkyl ether is DME (dimethylether).

In one embodiment the flow of gaseous hydrocarbon, alkyl alcohol or alkyl ether is applied for around 1-5 hours, e.g. 2 hours.

In one embodiment, the third step of the process involves that the silica or alumina and metal nanoparticles is heated (maybe 300-1100° C.) in a stream of a simple hydrocarbon gas (1-8 carbon atoms or cyclic hydrocarbons) that decomposes on the metal surface to leave the carbon template on the zeolite precursor composition. The layer of carbon protects the nanoparticles in the relatively harsh reaction (temperature, pressure, alkaline) that are necessary to grow the zeolite.

The fourth step involves two steps; step 4a is adding a structure directing agent to the carbon template coated zeolite, zeolite-like or zeotype precursor composition thereby creating a zeolite, zeolite-like or zeotype gel composition; and step 4b is crstallization of the zeolite, zeolite-like or zeotype gel composition by subjecting the zeolite, zeolite-like or zeotype gel composition to a hydrothermal treatment.

During this step 4, the silica/aluminium is dissolved in an aqueous alkaline media creating a supersaturated solution from which the zeolite is formed around the carbon template in the presence of a structure directing agent (SDA), preferably a quaternary ammonium salt such as TPAOH (tetrapropylammonium hydroxide) or TBAOH (tetrabutylammonium hydroxide). This creates an initial, amorphous zeolite gel, which in a subsequent hydrothermal step is transformed into the crystalline zeolite. The hydrothermal process is often performed under elevated temperatures between 70 and 300° C., preferably at 180° C., and autogeneous pressure in an autoclave or open flask for 24 hours or more.

A hydrothermal process is a technique of crystallizing substances from high-temperature aqueous solutions at high vapour pressure.

In one or more embodiments, the carbon template coated zeolite, zeolite-like or zeotype precursor composition of step 3 is used directly in step 4a without removing the silica or alumina source. In this way, the silica or alumina source is reused in the following process, which reduces the production cost compared to alternative processes, where it is removed and only the carbon skeleton is used in the further process as seen in e.g. A. H. Janssen et al, Microporous and Mesoporous Materials 65 (2003), page 59-75. Further, by reusing the silica or alumina source, the method is simplified.

In a specific embodiment, the fourth step comprises a hydrothermal treatment of the initially formed zeolite gel wherein the gel is heated to temperatures between 70 and 300° C., preferably at 180° C. In addition it may be under an autogeneous pressure in an autoclave or open flask for 24 hours or more.

In one embodiment the method of producing zeolite or zeotype encapsulated metal nanoparticles comprises adding an Al, Sn, Ti, Zr or Ge source during step 4a. The source may be an $Al^{3+}$, $Sn^{2+}$, $Sn^{4+}$, $Ti^{4+}$, Zr or Ge source. Sources of Titanium could be e.g. titanium chlorides, titanium sulphates, titanium alkoxides e.g. TEOT (tetraethyl orthotitanate) and TBOT (tetrabutyl orthotitanat). Sources of aluminium could be aluminum nitrate, aluminum sulphate, aluminum phosphate, sodium aluminate ect. Sources of tin could be tin chlorides, tin oxides or solid tin dissolved in hydrochloric acid. Sources of zirconia could be zirconia chloride or zirconia oxide. If an aluminium source was used in step 1 in the process instead of a silica source, then a silica source should be applied at this step. The source of silica is bulk silica of different quality and alumina contamination, including pure silica, fumed silica, sodium silicate or precipitated silica, tetraethyl orthosilicate ect.

The source of $Al^{3+}$, $Sn^{2+}$, $Sn^{4+}$, $Ti^{4+}$, Zr or Ge will be part of the framework in the crystal structure. Therefore, Ti-zeotype particles, Sn-zeotype particle, Zr-zeotype particle or Ge-zeotype particles can be manufactured by the present method.

In the fifth step the catalyst is washed, dried and calcined in air at above 300° C., preferably between 300-700° C., preferably between 400-700° C. to remove the structure directing agent and the carbon template. More preferably a controlled combustion is conducted by calcination the crystalized zeolite in air at 550° C. The combustion is conducted for e.g. 24 hours or 20 hours. Upon removal of the carbon template, by calcination, the zeolite crystals obtain a secondary porosity, in addition to the inherent zeolite microporous system. The porosity can be modified by changing the type and amount of carbon.

According to the present invention, the metal nanoparticles previously supporting the growth of carbon templates (whiskers, nanotubes etc) during the third step of the process are left behind in the secondary porosity of the zeolites after the fifth step has been carried out. These metal nanoparticles are homogeneously distributed throughout the crystalline zeolite structure and are further individually shielded from physical contact with other metal nanoparticles hosted in the zeolite by the walls of the formed pores. The metal nanoparticles remain accessible through the porous structure of the zeolites, however, but are thus protected from sintering with other nanoparticles at elevated temperatures due to said physical separation.

The calcination procedure conducted in step 5 is expected to remove the carbon template and remaining amounts of the structure directing agent. However, under certain combinations of reaction parameters the isolated encapsulated metal nanoparticles may still contain traces of carbon trapped in the zeolite structure which may influence the eventual activity and/or selectivity of the metal nanoparticles.

In the following one possible method is outlined. The first step involves that an aqueous solution of a metal nitrate is impregnated on the silica. The metal nitrate is then reduced in a hydrogen stream to form metal nanoparticles. Subsequently, the gas flow is exchanged and a carbon gas, e.g. propene gas is passed over the sample. Depending on the nature of the metal nanoparticles, the time of exposure to the hydrocarbon gas, the temperature, the carbon gas, e.g. propene may cover and encapsulate the metal nanoparticles or deposit as carbon [42, 43]. After this procedure, the zeolite precursor is mixed with a structuring directing agent (SDA) and $OH^-$ and put in a Teflon beaker inside a Teflon-lined autoclave containing a sufficient amount of water to generate saturated steam and heated to e.g. 180° C. for e.g. 72 hours. After the hydrothermal treatment, the carbon template is removed by combustion. This will lead to uniformed micropores or mesopores in the zeolite, which are modifiable by increasing or decreasing the nanoparticle size.

In one embodiment of the method the carbon template is shaped as carbon nanotubes.

Carbon formation in the form of whisker carbon is a very common phenomenon with e.g. nickel nanoparticles [42, 43]. This might resort to a larger amount of carbon formation than expected if the nanoparticles where simply encapsulated. The length, width and amount of carbon, e.g. in the form of whiskers, can be tuned by changing the different parameters, such as gas, temperature and time.

In one embodiment of the method the one or more metal precursors is loaded to the silica or alumina in an amount of 0.5 to 20 wt %, from 0.5 to 5 wt %, from 0.5 to 2 wt %, or around 1 wt % during step 1.

In one embodiment of the method the zeolite precursor has a carbon-to-silica ratio of from 0.30 to 2.00 w/w, 0.30 to 1.00 w/w, 1.00 to 2.00 w/w or from 0.34 to 0.75 w/w.

In one embodiment of the method the zeolite precursor has a carbon-to-alumina ratio of from 0.30 to 2.00 w/w, 0.30 to 1.00 w/w, 1.00 to 2.00 w/w or from 0.34 to 0.75 w/w.

EDS analysis of the calcined zeolite showed presence of nickel, titanium, oxygen and silicon.

The present invention also relates to a zeolite, zeolite-like or zeotype encapsulated metal nanoparticles manufactured by the method according to the present invention.

The physical and chemical properties of the zeolite material are modified by having the encapsulated nanoparticles within the pore system of the zeolite crystal.

In one embodiment, the encapsulated metal nanoparticles are sinter-resistant.

In one embodiment the particle is a hierarchical mesoporous zeolite, zeolite-like or zeotype particle.

In one embodiment the particles comprises mesopores in the range from 2 to 50 nm, from 5 to 30 nm, from 10 to 25 nm, from 15 to 25 nm, from 18 to 22 nm, from 19 to 21 nm or around 20 nm. In one embodiment the particles comprises mesopores having sizes around 10 nm.

In one embodiment the zeolite particles comprises micropores in the range from 0.1 to 2 nm, from 1 to 2 nm or around 2 nm.

In one embodiment the encapsulated metal nanoparticles comprise one or more metal(s) selected from the group consisting of group 4 elements, group 6 elements, group 7 elements, group 8 elements, group 9 elements, group 10 elements, group 11 elements or group 12 elements or mixtures thereof. The group elements are defined by the new IUPAC numbering.

In one embodiment the encapsulated metal nanoparticles comprise one or more metal(s) selected from the group consisting of titanium, osmium, iridium, platinum, ruthenium, palladium, rhodium, rhenium, copper, nickel, iron, cobalt, silver, gold, cadmium, molybdenium or mixtures thereof. In one embodiment the metal is nickel.

In one embodiment the size of the crystal structure are in the range of 1.0 to 2.5 µm.

In one embodiment the metal nanoparticles are immobilized in the zeolite or zeotype.

In one embodiment the zeolite, zeolite-like or zeotype encapsulated metal nanoparticles comprise an Al, Sn, Ti, Zr or Ge source in the framework of the crystal structure. The source may be an $Al^{3+}$, $Sn^{2+}$, $Sn^{4+}$, $Ti^{4+}$, Zr or Ge source. The source of $Al^{3+}$, $Sn^{2+}$, Se, $Ti^{4+}$, Zr or Ge will be part of the framework in the crystal structure. Therefore, the invention also comprise Ti-zeotype particles, Sn-zeotype particle, Zr-zeotype particle or Ge-zeotype particles manufactured by the present method.

In one embodiment the amount of metal nanoparticles are in the range of 0.1 to 25 wt %, in the range from 0.5 to 20 wt %, from 0.5 to 10 wt %, from 0.5 to 5%, from 1.0 to 5 wt %, from 1 to 2 wt %, or around 1 wt %.

The amount of metal nanoparticles in the crystallised zeolite structure is preferably more than 80% of the metal loading.

In one embodiment the zeolite, zeolite-like or zeotype particle has a Vp value in the range of 0.300 to 0.500 $cm^3/g$, 0.300 to 0.400 $cm^3/g$ or around 0.320 $cm^3/g$, or around 0.450 $cm^3/g$.

In one embodiment the zeolite, zeolite-like or zeotype particle has an external surface area in the range of 100-400 $m^2/g$, or around 170 to 200 $m^2/g$ or around 190 $m^2/g$.

In one embodiment the zeolite, zeolite-like or zeotype particle has a BET surface area of 300 to 500 $m^2/g$ or 350 to 400 $m^2/g$.

The zeolite, zeolite-like or zeotype encapsulated nanoparticles of the invention can be used as catalytic material for chemical reactions.

The invention also relates to the use of the zeolite, zeolite-like or zeotype encapsulated metal nanoparticles of the present invention in shape-selective catalysis.

Experimental Details

Methods for Characterisation—X-ray Powder Diffraction

XRPD is a widely used analytic method for structural characterization of crystalline materials. It is used to identify crystal structure and detect impurity phases. The method is based on diffraction, which occurs when an incident radiation interacts with an ordered solid and the wavelength of the electron magnetic radiation is in the same order as the distance between the crystal planes. Most often, the zeolite is analysed in the form of a powder and the obtained powder X-ray diffractogram can be used as a fingerprint unique to the particullar crystalline phase. Due to the small amount of titanium in the sample, it will be difficult to discern by XRPD, whether $TiO_2$ has formed. X-ray powder diffraction patterns (XRPD) was measured in transmission mode using Cu—Kα radiation from a focusing quartz monochromator and a HUBER G670 Guinier camara.

Methods for Characterisation—Scanning Electron Microscopy (SEM)

This analytic technique uses a finely focused high energy beam of electrons are is directed onto the surface of a sample. The electrons which are reflected by the surface and emitted secondary electrons, are detected to give a map of the surface topography of the sample. The samples may need to be applied with a conductive coating such as gold or graphite, to hinder local surface charging which leads to a decreased quality of SEM images [79].

Methods for Characterisation—Transmission Electron Microscopy (TEM)

TEM is a microscopy technique in which a beam of electrons is transmitted through an ultra-thin specimen, interacting with the specimen as it passes through. An image is formed from the interaction of the electrons transmitted through the specimen; the image is magnified and focused onto an imaging device, such as a fluorescent screen, on a layer of photographic film, or to be detected by a sensor such as a CCD camera.

Methods for Characterisation—Energy Dispersive X-ray Spectroscopy

In electron microscopy, the elements present in the sample emit characteristic X-rays due to the incident electron beam. These X-rays can be analysed to give a spectrum, and from there give both qualitative and quantitative results of the elements present [79]. Several precautions must however be made, as it is nigh impossible to get accurate quantitative results with this method on samples such as zeolites. This is because the accuracy of the spectrum is affected by the nature of the sample. X-rays are generated by any atom in the sample that is sufficiently excited by the incident electron beam. The X-rays are emitted in any direction, and so they may not all escape the sample. The likelihood of a X-ray escaping the sample, depends on the energy of the X-ray and the amount and density of material it has to pass through. This can result in reduced accuracy in porous and rough samples. As zeolites present are porous, the EDS results must be interpreted with caution, and are therefore only used qualitatively. SEM and EDS analysis were performed on a Quanta 200 ESEM FEG. The calcined zeolite samples were placed on a carbon film.

Methods for Characterisation—Nitrogen Physisorption

Key parameters for a solid catalyst is the accessibilty of the active sites for reactants. A conventional way of measuring this is by physisorption of nitrogen gas at 77 K. This method provides information on both surface area and pore size distribution in the micro-, meso- and macroporous range. The method is a stepwise adsorption of $N_2$ which first forms a monolayer, as the pressure of $N_2$ increases multi layers begin to form. The $N_2$ physisorption isotherms generated are very distinct, and classified into six types by IUPAC [80] which are presented in FIG. 3. Nitrogen physisorption of microporous solids, such as zeolites, result typically in Type I isotherms. They are characterised by the limiting uptake, which happens at relative low pressure and is controlled by the accessible micropore volume, and not the internal surface area. Type IV isotherms are most common when analysing mesoporous materials. The hysteresis loop between the adsorption and desorption branches, is a very characteristic feature for this type of isotherm, and is attributed to capillary condensation taking place in mesopores. Type II, III, V and VI are not commonly observed for zeolite materials, since they are typical for non-porous, macroporous or materials with weak forces of adsorption [80].

Nitrogen adsorption and desorption measurements were performed at liquid nitrogen temperature (77 K) on a Micromeritics ASAP 2420. The samples were outgassed in vacuum at 300° C., 16 hours prior to measurement. The total surface areas were calculated according to the BET method. Pore size distributions were calculated with BJH method. External surface area, micropore area and micropore volume were determined by t-plot methods in the desorption branch. Total pore volume was calculated for pores around 80 nm width at $p/p0=0.97$.

Methods for Characterisation—Diffuse Reflectance UV-Vis Spectroscopy

By exposing molecules to radiation in the ultraviolet-visible (UV-Vis) spectral region, spectroscopy can be applied to determine the concentration of an analyte. However, important characteristics of the sample are obtainable. It is possible to detect and determine the coordination environment of d-d transitions in the sample, and metal-ligand complexes due to the specific energy required to excite them. However, in the case of powdered catalyst samples, the incident light can not penetrate the sample and is almost completely diffused. It is therefore not possible to use transmission spectroscopy, instead diffuse reflectance (DR) spectroscopy has to be applied. Overall, this method can serve as a great asset in determining which titanium species is present in the produced catalysts. DR UV-Vis spectra were obtained with a CARY 5000 spectrometer employing spectralon® as internal standard.

Materials

Mesoporous silica (Merck, silica gel 100, particle size 0.063-0.200 mm, pore diameter 15 nm, pore volume 1.15 ml/g), was used for the synthesis of mesoporous zeolites involving metal nanoparticles. The silica were dried at 80° C. for 24 hours prior to use. All other reagents were of reagent grade and used without further purifications: tetraethylorthosilicate (TEOS, 98 wt %, Aldrich), tetraethylorthotitanate (TEOT, 98 wt %, Aldrich), tetrapropylammonium hydroxide (TPAOH, 40 wt %, Fluka), hydrogen peroxide ($H_2O_2$, 40 wt %, Aldrich).

Synthesis—Propene Based Method

The zeolites prepared by the new synthesis method disclosed in this application may be prepared by the following method using propene to form the carbon template coated zeolite, zeolite-like or zeotype precursor composition: First, 2.5 grams of silica is impregnated to incipient wetness with a metal nitrate solution, eg. nickel nitrate. This is allowed to stand at 80° C. overnight. The solid is subsequently placed in a tube oven and heated to 600° C. in argon flow. A gas mixture of 10% hydrogen in nitrogen is then led over for a total of 4 hours. The temperature is afterwards reduced to 550° C. under argon atmosphere. As an alternative to reducing the temperature to 550° C. under argon atmosphere, it may be increased to 700° C. still under argon atmosphere.

Propene gas is subsequently applied for 2 hours, afterwards a low flow of argon is led over, while the sample is allowed to cool off. Pure silica did not change colour during the procedure, while both nickel- and iron nitrate on silica were completely black after the treatment.

A mixture of 16.915 g 20% TPAOH, 4.25 ml water, 0.265 g NaOH and 0.095 g TEOT is prepared and stirred until a clear solution was obtained. The silica-carbon composite is added and left for 1 hour. The gel is then introduced into a stainless steel autoclave which is heated to 180° C. for 72 hours. Afterwards it is filtrated until the rinse water is neutral. The solid is left overnight at room temperature, followed by calcination at 550° C. for 24 hours. Zeolites made by this method are nominated Metal-C/SiO2 ratio-TS-1, e.g. Ni-0.74-TS-1.

The above synthesized zeolite is in the following compared to other mesoporous catalysts prepared through carbon templating and desilication (results presented in FIGS. 4-6 and 8-14). This is done to determine the influence the synthesis method has on active species in the catalyst, as well as the effect on the external surface area, and the ability to introduce mesoporosity in addition to the microporosity found in conventional zeolites.

In the following, conventional TS-1 catalysts are denoted TS-1 and mesoporous carbon-templated TS-1 (1% Ti) are denoted cTS-1. A conventional TS-1 that has been desilicated is denoted dTS-1 and TS-1 that has been prepared with BP-2000 and desilicated is named cdTS-1.

Characterization of Catalysts—Carbon Uptake with Propene Method

Several experiments were done to test the carbon loading with different parameters. After the carbon loading, several were synthesised to either HZSM-5, TS-1 or both. Table 1 shows the carbon uptake in a carbon-to-silica ratio (on weight basis) with different metals and parameters. Pure silica took up no amount of carbon, which also was proven by the absence of colour change after the propene procedure. The following zeolite synthesis was abandoned, as this would only create a conventional zeolite. The carbon uptake on nickel-$SiO_2$ was proven to be modifiable by both changing the metal loading and the flow of propene. An increase in nickel loading, also increased the carbon uptake, with a linear correlation. By changing the flow of propene, it was possible to modify the carbon uptake to some extent. An increase in flow from 51 ml/min to 67 ml/min resulted in a raise of $C/SiO_2$ ratio from 0.34 to 0.74. This was not increased further by another raise in flow speed. Iron showed a very limited uptake with a $C/SiO_2$ ratio of 0.03. The silica was black after the propene treatment, confirming the uptake of carbon.

TABLE 1

Carbon uptake of silica with different metal loading and propene flow.

| Samples | Metal Loading [wt %] | Propene Flow [ml/min] | $C/SiO_2$ Ratio [w/w] |
|---|---|---|---|
| $SiO_2$ | — | 67 | 0 |
| Ni—$SiO_2$ | 1% | 51 | 0.34 |
| Ni—$SiO_2$ | 1% | 67 | 0.74 |
| Ni—$SiO_2$ | 1% | 85 | 0.75 |
| Ni—$SiO_2$ | 2% | 67 | 1.18 |
| Ni—$SiO_2$ | 5% | 67 | 2.13 |
| Fe—$SiO_2$ | 1% | 67 | 0.03 |

Characterization of Catalysts—XRPD

For comparison of crystallinity of the zeolite catalysts, XRPD patterns were recorded after synthesis and subsequent calcination. Patterns for all synthesised TS-1 catalysts are presented in FIG. 4. It is clear that the zeolite samples contain highly crystalline structure, with no impurities or amorphous phase present. It is difficult to discern if titanium is present in other confirmations than inside the framework, as the titanium content is very low. In addition, all patterns match the pattern of silicalite-1, confirming the MFI structure. The Ni-0.74-TS-1 catalyst produced by the synthesis method disclosed in this application (nickel-propene method), also underwent XRPD analysis. The result is present in FIG. 5. The catalyst exhibit the same characteristic pattern as samples with MFI structure. In addition, no amorphous phase or impurities were found present, and the sample was highly crystalline.

Characterization of Catalysts—Scanning Electron Microscopy (SEM)

All synthesised catalyst underwent analysis by SEM. This was done to investigate the morphology of the produced catalysts. In FIG. 6 conventional and mesoporous TS-1 are compared to the desilicated counterparts. Conventional TS-1, FIG. 6a, shows clearly defined cubic coffin shaped crystals with sizes of 0.2-0.4 μm. With crystals in this size range, the diffusion limitations have been decreased to a minimum, without introducing mesopores. Desilicated TS-1 are shown in FIG. 6b. It shows an agglomerate of smaller crystals, with no clear consistent structure or size. Compared to the conventional TS-1, the mesoporous sample in FIG. 6c is much bigger, with crystal sizes in the range of 1.5-2.5 μm. While the surface for the conventional TS-1 is very smooth, the mesoporous sample exhibits a more "sponge"-like shape. The desilicated mesoporous TS-1, FIG. 6d, shows some of the same characteristics as the other desilicated sample. These similarities are the agglomeration of smaller crystals, and no clear structure or size. The shape of the original mesoporous sample can however faintly be seen.

SEM images of the propene treated nickel and iron samples are shown in FIG. 7. The reason for the higher carbon uptake on the nickel samples are clear here. Several carbon nanofibers are present on the nickel sample, and absent on the iron sample. This was expected as, nickel is known for creating carbon whiskers at high temperatures in the presence of hydrocarbons [42]. To examine whether the iron nanoparticles were unchanged within the zeolite and encapsulated in carbon, TEM analysis will have to be done. TEM analysis will also be interesting, as to determine the size of the produced nanoparticles, both before and after synthesis.

FIG. 8 is a picture of the titanium containing zeolites prepared through the coking of nickel nanoparticles. The sample presented in FIG. 8, has a $C/SiO_2$ ratio=0.75, and showed mesoporosity visible with SEM. In addition, all silica was also converted to zeolites.

Characterization of Catalysts—Energy Dispersive X-ray Spectroscopy

EDS was used to qualitatively determine the elements present in the samples. All TS-1 catalysts synthesised showed the presence of titanium, silicon and oxygen. Furthermore the samples prepared through coking of nickel nanoparticles, also showed presence of nickel. To get an exact value of the nickel present in the sample, a method consisting of dissolution of the zeolite, followed by Inductively Coupled Plasma (ICP) could be applied.

Characterization of Catalysts—Nitrogen Physisorption

The textural properties of the synthesized materials were determined by adsorption-desorption analysis with nitrogen. The observed SBET, external surface areas, Sext, micropore and total pore volumes are collated in Table 2. The BET value is less for cdTS-1 and cTS-1. Logically the samples exhibit increasing external surface area after the introduction of mesoporosity. cTS-1 has the highest external surface, dTS-1 somewhat lower, and cdTS-1 curiously has a value which corresponds with the average of cTS-1 and dTS-1. The same is the case for the micropore volumes. FIG. 9 shows the isotherms of the samples. According to the IUPAC classification of physisorption isotherms, the conventional TS-1 has a type I isotherm with a sharp transition in the adsorption branch at $P/P_0<0.1$ and almost no adsorption at intermediate relative pressures. This is typical for purely microporous materials such as zeolites.

At $P/P_0>0.9$ further nitrogen uptake takes place due to the interparticle adsorption within the voids between the small zeolitic particles as observed in the SEM analysis for conventional TS-1. cTS-1, dTS-1 and cdTS-1 exhibit the type IV isotherms with clearly visible hysteresis loops, which are typical for mesoporous materials. The mesoporous samples created by carbon templating of TS-1, present hysteresis loops at $P/P_0>0.86$ and can be attributed to the interparticle adsorption within the voids formed between the zeolitic particles, or more likely due to creation of some very large pores, which would be in line with observation of large, SEM visible porosity in the cTS-1 sample. dTS-1 (and cdTS-1 to a smaller extent) show smaller hysteresis loop closing at $P/P_0>0.42$ with less generation of mesopores compared to micropores. These could be from the voids existing between the nanocrystallites due to the desilication, but they are more likely to originate from the so-called TSE-effect [81, 82] where capillary evaporation during desorption occurs via a hemispherical meniscus, separating the vapour and the capillary condensed phase [83].

TABLE 2

Nitrogen physisorption data for the investigated catalysts.

| Sample | $S_{BET}$ m²/g | $S_{ext}$ m²/g | $V_{Micro}$ cm³/g | $V_p$ cm³/g |
|---|---|---|---|---|
| TS-1 | 390 | 166 | 0.0915 | 0.224 |
| dTS-1 | 346 | 225 | 0.0498 | 0.478 |
| cTS-1 | 367 | 136 | 0.0981 | 0.448 |
| cdTS-1 | 353 | 182 | 0.0731 | 0.622 |

Barrett-Joyner-Halenda (BJH) analysis of desorption branch further indicate secondary a mesopore distributions in the TS-1 derived catalysts. This mesoporosity is created at the expense of the decrease of micropore volume as seen in Table 2, especially for cTS-1 and cdTS-1, and an increase of the external surface compared to the value of TS-1 as mentioned above. For cTS-1 calcination of carbon template create mesoporous of around 19 nm and around 59 nm for cdTS-1. The dTS-1 catalyst exhibits mesopores around 60 nm but in lesser amount as shown in FIG. 10.

The zeolite prepared trough coking of nickel nanoparticles, Ni-0.74-TS-1, was also characterised with nitrogen physisorption. FIG. 11 shows the adsorption/desorption isotherms of the zeolite. The sample shows a clear type IV isotherm, with hysteresis loops at $P/P_0>0.80$, most likely to originate from mesopores. The hysteresis loop around $P/P_0>0.18$, has still yet to be assigned to a structural property. The BJH pore size distribution, FIG. 12, confirms the presence of mesopores of the same size (19 nm) as the carbon templated TS-1, but in a much smaller magnitude. In addition, the size of the micropores are slightly smaller than the conventional TS-1, and similar to the TS-1 zeolites prepared by carbon templated. The mesoporosity of the Ni-0.74-TS-1 is also confirmed by the Vp result presented in Table 3. With a value of 0.323 cm³/g, this is nearly 1.5 times greater than the conventional TS-1 synthesised. In addition, the external surface area of Ni-0.74-TS-1, is also larger, at 189 m²/g compared to 166m²/g of the conventional TS-1.

TABLE 3

Nitrogen physisorption data for the synthesised Ni-0.74-TS-1.

| Sample | $S_{BET}$ m²/g | $S_{ext}$ m²/g | $V_{Micro}$ cm³/g | $V_p$ cm³/g |
|---|---|---|---|---|
| Ni-0.74-TS-1 | 400 | 189 | 0.0854 | 0.323 |

Characterization of Catalysts—Diffuse Reflectance UV-Vis Spectroscopy

FIG. 13 shows the results of the DR-UV-Vis spectroscopy. TS-1 shows a maximum at 47600 cm⁻¹ (210 nm), which is characteristic from the charge transfer of oxygen 2p electron to the empty 3d orbit of framework Ti species in tetrahedral coordination. This band is known as a fingerprint of tetrahedrally coordinated Ti(OSi)$_4$ species in titanium silicate frameworks. The slightly shift to higher wavelengths. at ca. 45500 cm⁻¹ (220 nm) for the desilicated samples suggests the simultaneous presence of tetrahedral tripodal Ti(OSi)$_3$OH and tetrapodal Ti(OSi)$_4$. This might be a due to an increased surface density of Ti⁴⁺, due to the desilication process. This effect is only apparent in the desilicated samples, cdTS-1 and dTS-1.

Furthermore, dTS-1 shows a broad band at 38400-33300 cm⁻¹ (260-300 nm) that can be attributed to the partially polymerized hexacoordinated non-framework Ti species, which contain Ti—O—Ti bonds [84, 85]. This strongly suggest a densitification of titania species, most likely on the outside of the zeolite framework. In addition, cTS-1 and cdTS-1 also shows a broad band between 31250-29400 cm⁻¹ (320-340 nm), which is typical for larger extraframework TiO$_2$ particles with a structure similar to anatase. This suggest that the carbon-templating technique might also interfere with the active titania sites to some degree, perhaps by provoking some agglomeration of titania species near the mesopore channels, which could be thought to occur from the creation of hotspots during the carbon burnout. Overall, the titania species appear less harmed by the carbon-template method compared to the desilication method.

For an easier comparison, TS-1 is also shown in FIG. 14. Ni-0.74-TS-1 shows a maximum at around 47600 cm⁻¹ (210 nm), just as conventional TS-1. In addition it shows the same tendency to absorb in the broad band between 31250-29400 cm⁻¹ (320-340 nm), just like the other carbon templated zeolites.

Synthesis—Methane Based Method

As an alternative to the propene based synthesis shown and discussed above, the zeolites prepared by the new synthesis method disclosed in this application may be prepared by the following method using methane to form the carbon template coated zeolite, zeolite-like or zeotype precursor composition: First, 5 grams of silica are impregnated to incipient wetness with a nickel nitrate solution. The resulting materials typically contained around 2 wt % of Ni metal. This is allowed to stand overnight. The solid is then placed in a tube oven and heated to 600° C. in argon flow, with a subsequent change of gas to 10% hydrogen in nitrogen for 4 hours. The temperature is reduced to 550° C. under argon. As an alternative to reducing the temperature to 550° C. under argon atmosphere, it may be increased to 700° C. still under argon atmosphere.

Methane gas is then applied for between 10 minutes and up to 12 hours. Preferably, methane is added for between 2-8 hours, or approximately 6 hours if the temperature is kept at 550° C. If the temperature is kept at 700° C., methane is normally applied for a shorter time of 10 minutes to 4 hours, or for 2-3 hours. Afterwards, the oven is cooled to room temperature with a flow of Ar.

In a 20 ml Teflon beaker 0.5 g of the materials from above are impregnated with 2.95 ml of 20% TPAOH (tetrapropylammonium hydroxide) solution. 10-20 ml of water is introduced to a 300 ml stainless steel autoclave. The Teflon beaker is placed in the water in the bottom of the autoclave. The closed autoclave is heated to 180° C. for 72 hours. Afterwards, the solid is washed with demineralized water. The zeolite/carbon composition is then heated to 550° C. for 24 hours to remove the carbon.

The TEM image of the above zeolite produced using methane, where the material is heated to 550° C. under argon before methane gas is added, is displayed in FIG. 15.

The SEM image of the above zeolite produced using methane, where the material is heated to 700° C. under argon before methane gas is added, is displayed in FIG. 16.

In FIG. 17a and FIG. 17b, the XRPD pattern of MFI zeolite synthesized using methane is displayed, where FIG. 17a represents a synthesis method, where the material is heated to 550° C. under argon before methane gas is added and FIG. 17b represents a synthesis method, where the material is heated to 700° C. under argon before methane gas is added.

As can be seen when comparing FIG. 5 with FIG. 17a and FIG. 17b, very little variation is observed in the XRPD pattern depending on which gaseous hydrocarbon that is used in the synthesis and at which temperature the sample is heated.

REFERENCES

[1] R. W. Broach, D. Jan, D. A. Lesch, S. Kulprathipanja, E. Roland, and P. Kleinschmit. Zeolites. In *Ullmann's Encyclopedia Of Industrial Chemistry*. Wiley, 2012.
[2] Szostak, Rosemarie. Molecular Sieves Principles of Synthesis and Identification. New York: Van Nostrand Reinhold, 1989
[3] J. Cejka and D. Kubicka. Zeolites and other micro- and mesoporous molecular sieves. In *Kirk-Othmer Encyclopedia of Chemical Technology*. Wiley, 2010.
[4] K. Egeblad. *Conversion of Oxygenates over Zeolite Catalysts: Structure-Activity Relations*. PhD thesis, 2011.
[37] C. J. H. Jacobsen and C. Madsen. Mesoporous zeolite single crystals. *J. Am. Chem. Soc.*, page 7116, 2000.
[38] K. Zhu, K. Egeblad, and C. H. Christensen. *Stud. Surf. Sci. Catal.*, 172:285, 2008.
[39] I. Schmidt, A. Boisen, E. Gustaysson, K. St°ahl, S. Pehrson, S. Dahl, A. Carlsson, and C. J. H. Jacobsen. *Chem. Mater.*, 13:4416, 2001.
[41] M. Kustova, K. Egeblad, K. Zhu, and C. H. Christensen. *Chem. Mater.*, 19:2915, 2007.
[42] J. Sehested. *Catal. Today*, 111:103, 2006.
[43] A. K. Rovik, S. K. Klitgaard, S. Dahl, C. H. Christensen, and I. Chorkendorff. *Appl. Catal. A-Gen*, 358:269, 2009.
[45] P. M. Arnal, M. Comotti, and F. Schuth. *Angew. Chem. Int. Ed.*, 45:8224, 2006.
[46] N. Ren and Y.-H. Yang and. *J. Catal.*, 251:182, 2007.
[47] S. H. Joo, J. Y. Park, C.-K. Tsung, Y. Yamada, and P. Yang. *Nature Mater.*, 8:126, 2009.
[48] L. W. Beakley, S. E. Yost, R. Cheng, and B. D. Chandler. *Appl. Catal. A*, 292:124, 2005.
[49] T. M. Salama, R. Ohnishi, T. Shido, and M. Ichikawa. *J. Catal.*, 156:169, 1996.
[50] Y.-M. Kang and B.-Z. Wan. *Appl. Catal. A: General*, 128:53, 1995.

[51] Z. X. Gao, Q. Sun, H.-Y. Chen, X. Wang, and W. M. H. Sachtler. *Catal. Lett.,* 2001:1, 72.
[52] A. B. Laursen, K. T. Højholt, L. F. Lundegaard, S. B. Simonsen, S. Helveg, F. Schuth, M. Paul, J.-D. Grunwaldt, S. Kegæs, C. H. Christensen, and K. Egeblad. *Angew. Chem. Int. Edit.,* 122:3582, 2010.
[53] K. T. Højholt, A. B. Laursen, S. Kegæs, and C. H. Christensen. *Top. Catal.,* 54:1026, 2011.
[56] Marco Taramasso, Giovanni Perego, and Bruno Notari. Taramasso U.S. Pat. No. 4,410,501, 1983.
[57] S. Bordiga, F. Bonino, A. Damin, and C. Lamberti. *Phys. Chem. Chem. Phys.,* 9:4854, 2007.
[58] G. N. Vayssilov. *Catal. Rev.,* 39:209, 1997.
[59] R. J. Saxton. *Top. Catal.,* 9:43, 1999.
[60] F. Cavani and J. H. Teles. *ChemSusChem,* 2:508, 2009.
[61] A. Corma and H. Garcia. *Chem. Rev.,* 102:3837, 2002.
[79] L. E. Smart and E. A. Moore. *Solid State Chemistry—An Introduction.* CRC Press, $3^{rd}$ edition edition, 2005.
[80] K. S. W. Sing. *Pure & Appl. Chem.,* 54:2201, 1982.
[81] O. Kadlec and M. M. Dubinin. *J. Colloid Interface Sci.,* 31:479, 1969.
[82] C. V. G. Burgess and D. H. Everett. *J. Colloid Interface Sci.,* 33:611, 1970.
[83] J. C. Groen, L. A. A. Peffer, and J. P'erez-Ram'irez. *Micropor. and Mesopor. Mater.,* 60:1, 2003.
[84] P. Ratnasamy, D. Srinivas, and H. Knazinger. *Adv. Catal.,* 48:1, 2004.
[85] G. Petrini, A. Cesana, G. De Alberti, F. Genoni, G. Leofanti, M. Padovan, G. Paparatto, and P. Rofia. *Stud. Surf. Sci. Catal.,* 68:761, 1991.
[93] High-Temperature-Stable Catalysts by Hollow Sphere Encapsulation, P. M. Arnal, M. Comotti, F. Schüth, Angew. Chem. 2006, 118, 8404-8407.
[94] A Highly Reactive and Sinter-Resistant Catalytic System Based on Platinum Nanoparticles Embedded in the Inner Surfaces of $CeO_2$ Hollow Fibers, Y. Dai, B. Lim, Y. Yang, C. M. Cobley, W. Li, E. C. Cho, B. Grayson, P. T. Fanson, C. T. Campbell, Y. Sun, and Y. Xia, Angew. Chem. Int. Ed. 2010, 49, 1-5.
[95] Encapsulation of Metal (Au, Ag, Pt) Nanoparticles into Mesoporous SBA-15 structure, J. Zhu, Z. Kónya, V. F. Puntes, I. Kiricsi, C. X. Miao, J. W. Agar, A. Paul Alivisatos, G. A. Somorjai, Langmuir 2003, 19, 4396-4410.
[96] Cobalt nanoparticles prepared in faujasite zeolites by borohydride redction, Y. Wang, H. Wu, Q. Zhang, Q. Tang, Microporous and Mesoporous Materials 2005, 86, 38-49.
[97] Encapsulation of Transition Metal Species into Zeolites and Molecular Sieves as Redox Catalysts—Part 1, X. S. Zhao, G. Q. Lu, G. J. Millar, Journal of Porous Materials 1996, 3, 61-66.
[98] Preparation of Hollow Zeolite Spheres and Three-Dimensionally Ordered Macroporous Zeolite Monoliths with Functionalized Interiors, A. Dong, N. Ren, W. Yang, Y. Zhang, D. Wang, J. Hu, Z. Gao, Y. Tang, Adv. Funct. Mater. 2003, 13, 943-948.
[99] Redox Behavier of $SnO2$ Nanoparticles Encapsulated in the Pores of Zeolites, M. Warnken, K. Lázar, M. Wark, Phys. Chem. Chem. Phys. 2001, 3, 1870-1876.

The invention claimed is:

1. A method for producing zeolite, zeolite-like or zeotype encapsulated metal nanoparticles, comprising:
1) Adding one or more metal precursors to a silica or alumina source;
2) Reducing the one or more metal precursors to form metal nanoparticles supported on the surface of the silica or alumina source;
3) Passing a gaseous hydrocarbon, alkyl alcohol or alkyl ether over the metal nanoparticles supported on the surface of the silica or alumina source to form a zeolite, zeolite-like or zeotype precursor composition comprising carbon template coated metal nanoparticles;
4a) Dissolving the zeolite, zeolite-like or zeotype precursor composition comprising carbon template coated metal nanoparticles in an aqueous alkaline media and adding a structure directing agent thereby creating a zeolite, zeolite-like or zeotype gel composition;
4b) Crystallising the zeolite, zeolite-like or zeotype gel composition by subjecting said composition to a hydrothermal treatment; and
5) Removing the carbon template and structure directing agent and isolating the resulting zeolite, zeolite-like or zeotype encapsulated metal nanoparticles;
wherein the zeolite, zeolite-like or zeotype precursor composition comprising carbon template coated metal nanoparticles of step 3 is used directly in step 4a without removing the silica or alumina source; and
wherein step 1 is performed at a temperature between 50 and 150° C.

2. The method for producing zeolite, zeolite-like or zeotype encapsulated metal nanoparticles according to claim 1, wherein the one or more metal(s) is selected from the group consisting of group 4 elements, group 6 elements, group 7 elements, group 8 elements, group 9 elements, group 10 elements, group 11 elements and group 12 elements or mixtures thereof.

3. The method for producing zeolite, zeolite-like or zeotype encapsulated metal nanoparticles according to claim 1, wherein the one or more metal(s) is selected from the group consisting of titanium, osmium, iridium, platinum, ruthenium, palladium, rhodium, rhenium, copper, nickel, iron, cobalt, silver, gold, cadmium, and molybdenium or mixtures thereof.

4. The method for producing zeolite, zeolite-like or zeotype encapsulated metal nanoparticles according to claim 1, wherein the hydrocarbon is selected from the group consisting of aliphatic hydrocarbons having 1 to 8 carbon atoms, having 1 to 3 carbon atoms, alkenes having 2 to 6 carbon atoms, aromatic hydrocarbons having 6 to 10 carbon atoms and cyclic hydrocarbons having 3 to 8 carbon atoms.

5. The method for producing zeolite, zeolite-like or zeotype encapsulated metal nanoparticles according to claim 1, wherein the one or more metal precursor is loaded to the silica or alumina in an amount of from 0.5 to 20 wt %, from 0.5 to 5 wt %, from 0.5 to 2 wt %, or 1 wt % during step 1.

6. The method for producing zeolite, zeolite-like or zeotype encapsulated metal nanoparticles according to claim 1, comprising adding an Al, Sn Ti, Zr or Ge source during step 4a.

7. The method for producing zeolite, zeolite-like or zeotype particles according to claim 1, wherein the hydrothermal treatment comprises heating the zeolite, zeolite-like or zeotype gel composition to a temperature between 70 and 300° C., or 180° C., under an autogeneous pressure in an autoclave or open flask for 24 hours or more.

* * * * *